(12) United States Patent
Pacak et al.

(10) Patent No.: US 10,524,829 B2
(45) Date of Patent: Jan. 7, 2020

(54) TROCAR SUPPORT

(71) Applicant: Surgical Stabilization Technologies Inc., Winnipeg (CA)

(72) Inventors: John Stephen Pacak, Winnipeg (CA); Heather Dawn Diamond, Winnipeg (CA); Damian Raymond Muldoon, County Galway (IE); Shane Gerard Ward, Galway (IE); Brian Fergus Murphy, County Galway (IE); William James Cannon, County Galway (IE); Luke Patrick Keaveney, County Galway (IE)

(73) Assignee: Surgical Stabilization Technologies Inc., Winnipeg, MB (CA)

( * ) Notice: Subject to any disclaimer, the term of this patent is extended or adjusted under 35 U.S.C. 154(b) by 33 days.

(21) Appl. No.: 15/354,624

(22) Filed: Nov. 17, 2016

(65) Prior Publication Data
US 2017/0135721 A1 May 18, 2017
US 2019/0357937 A9 Nov. 28, 2019

Related U.S. Application Data

(63) Continuation-in-part of application No. 14/239,006, filed as application No. PCT/CA2012/050546 on Aug. 10, 2012, now Pat. No. 9,681,887.
(Continued)

(51) Int. Cl.
  *A61B 17/34* (2006.01)
  *A61B 17/02* (2006.01)
  *A61B 17/00* (2006.01)

(52) U.S. Cl.
  CPC .......... *A61B 17/34* (2013.01); *A61B 17/0218* (2013.01); *A61B 17/3403* (2013.01);
(Continued)

(58) Field of Classification Search
  CPC .. A61B 2017/3486; A61B 2017/00557; A61B 2017/3492; A61B 2017/00477;
(Continued)

(56) References Cited

U.S. PATENT DOCUMENTS

| 3,044,468 A | 7/1962 | Birtwell |
| 3,253,594 A | 5/1966 | Matthews |

(Continued)

FOREIGN PATENT DOCUMENTS

| CA | 2447100 | 5/2002 |
| EP | 2238924 | 3/2010 |

(Continued)

*Primary Examiner* — Kevin C Sirmons
*Assistant Examiner* — Tezita Z Watts
(74) *Attorney, Agent, or Firm* — Adrian D. Battison; Ade & Company Inc.; Michael R. Williams

(57) ABSTRACT

A support apparatus for supporting a trocar while the trocar extends through a body wall of a patient includes an inflatable collar and a slidable abutment collar commonly connected for engagement onto the trocar following which the slide collar is released to slide along the trocar. The inflatable collar is inflated to a set size by a manually operable pump on the slidable collar operated by squeezing finger abutments together up to a latch so that threaded portion expels the inflation fluid. The abutment member is shaped to be received on an outer surface of the trocar and adjustable longitudinally of the trocar sleeve so as to be located at a selected position by a manually movable latch collar. The inflatable collar and slidably collar are held connected by a manually operable release.

16 Claims, 19 Drawing Sheets

Related U.S. Application Data

(60) Provisional application No. 62/256,526, filed on Nov. 17, 2015, provisional application No. 61/524,470, filed on Aug. 17, 2011.

(52) U.S. Cl.
CPC ............... *A61B 2017/00477* (2013.01); *A61B 2017/00557* (2013.01); *A61B 2017/00862* (2013.01); *A61B 2017/0225* (2013.01); *A61B 2017/3407* (2013.01); *A61B 2017/3486* (2013.01)

(58) Field of Classification Search
CPC .. A61B 2017/00862; A61B 2017/0225; A61B 2017/3407; A61M 25/01; A61M 25/10
See application file for complete search history.

(56) References Cited

U.S. PATENT DOCUMENTS

| | | |
|---|---|---|
| 4,861,334 A | 8/1989 | Nawaz |
| 5,147,316 A | 9/1992 | Castillenti |
| 5,176,697 A | 1/1993 | Hasson |
| 5,290,249 A | 3/1994 | Foster |
| 5,338,302 A | 8/1994 | Hasson |
| 5,366,478 A | 11/1994 | Brinkerhoff et al. |
| 5,634,967 A | 6/1997 | Williams et al. |
| 5,728,119 A | 3/1998 | Smith |
| 7,597,688 B1 | 10/2009 | Masson |
| 7,998,113 B2 | 8/2011 | Swisher |
| 8,454,645 B2 | 6/2013 | Criscuolo |
| 8,888,692 B1 | 11/2014 | Pravongviengkham |
| 8,939,946 B2 | 1/2015 | Albrecht |
| 9,681,887 B2 | 6/2017 | Pacak |
| 2003/0139758 A1 | 7/2003 | Hopper et al. |
| 2004/0138702 A1 | 7/2004 | Peartree et al. |
| 2005/0113856 A1 | 5/2005 | Epstein |
| 2005/0165432 A1 | 7/2005 | Heinrich |
| 2006/0079918 A1 | 4/2006 | Creston |
| 2006/0135951 A1 | 6/2006 | Meek et al. |
| 2007/0213675 A1* | 9/2007 | Albrecht ............ A61B 17/3421 604/264 |
| 2007/0225650 A1 | 9/2007 | Hart et al. |
| 2007/0239108 A1 | 10/2007 | Albrecht et al. |
| 2009/0221960 A1 | 9/2009 | Albrecht et al. |
| 2010/0010449 A1 | 1/2010 | Leibowitz et al. |
| 2010/0081994 A1 | 4/2010 | Zisow |
| 2010/0152664 A1 | 6/2010 | Davis |
| 2010/0249524 A1 | 9/2010 | Ransden et al. |

FOREIGN PATENT DOCUMENTS

| | | |
|---|---|---|
| WO | 03094994 | 11/2003 |
| WO | 2007109700 | 9/2007 |
| WO | 2013023293 | 2/2013 |

\* cited by examiner

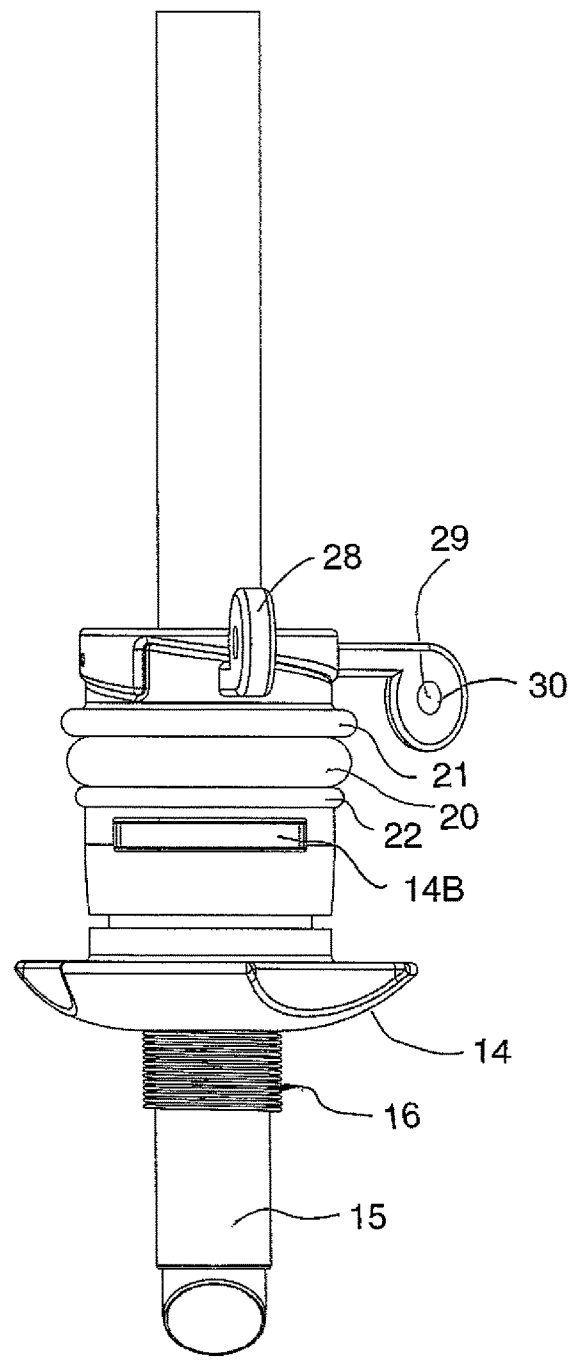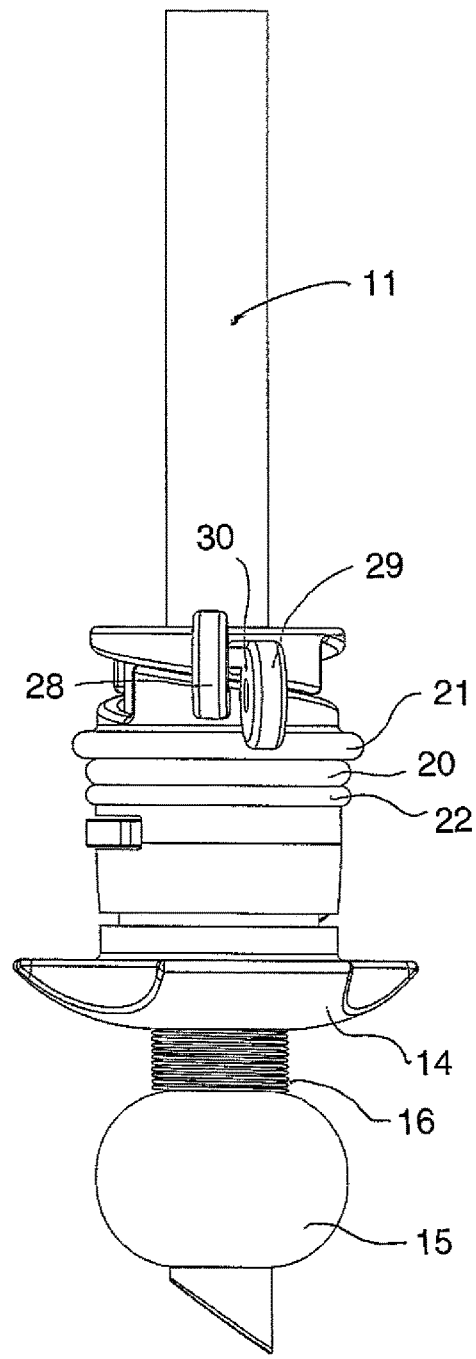
FIG. 2
FIG. 3

TROCAR SUPPORT

This application is a continuation in part application of application Ser. No. 14/239,006 now issued as U.S. Pat. No. 9,681,887 on Jun. 20, 2017 which is a 371 of PCT/CA2012/050546 filed Aug. 10, 2012 which claims benefit of Provisional application 61/524,470 filed Aug. 17, 2011. This application claims the benefit under 35 USC 119 (e) of Provisional application 62/256,526 filed Nov. 17, 2015.

This invention relates to an apparatus arranged to locate and hold a trocar in position through the wall of the body of the patient. A trocar is a tubular device which extends through a body wall of a patient to enable internal surgical procedures so that reference herein to a trocar is intended to include any such tubular device of this type.

BACKGROUND OF THE INVENTION

In published PCT application 2013/023293 published Feb. 21, 2013 of the present Applicant is shown a support apparatus for supporting a trocar while the trocar extends through a body wall of a patient includes an inflatable collar extending around the trocar which can be inflated to a predetermined size by a source of fluid where the source of fluid is located on the trocar support apparatus itself so as to be carried thereby and is defined by a pump mechanism to provide a fixed volume allowing inflation only to a fixed size. An abutment member is shaped to be received on an outer surface of the trocar sleeve and adjustable longitudinally of the trocar sleeve so as to be located at a selected position. A tube connecting the pump on the abutment to the inflatable collar is wrapped helically around the sleeve of the trocar.

SUMMARY OF THE INVENTION

It is one object of the invention to provide an improved trocar support of this general type.

According to one aspect of the invention there is provided a trocar support apparatus for use with a trocar separate from the apparatus for maintaining the trocar in fixed position in a body wall of a patient while the trocar extends through the body wall of a patient, the support comprising:

an annular expandable member for extending around the trocar, said annular expandable member being movable in an expansion movement from a collapsed condition radially outwardly of the trocar to a predetermined size;

an annular abutment collar arranged to be received on the trocar at a required position thereon;

the annular abutment collar being adjustable longitudinally of the trocar so as to be located at a selected position;

a releasable clamping member on the annular abutment collar for locating the annular abutment collar on the trocar at the selected position;

said annular expandable member being arranged while in said collapsed condition to be inserted through an incision in the body wall and expanded when inserted to engage an inside surface of the body wall;

wherein the annular expandable member is expandable by a manually operable device providing a source of the fluid mounted on the annular abutment collar;

wherein the manually operable device comprises a pair of annular members locating a fluid containing member therebetween, the annular members and the fluid containing member surrounding a central opening for passage therethrough of the trocar;

and a manually operable compression device for squeezing one annular member in an axial direction toward of the other annular member for expelling fluid from the fluid containing member.

According to another aspect of the invention, which can be used independently or in combination with the above, there is provided a trocar support apparatus for use with a trocar separate from the apparatus for maintaining the trocar in fixed position in a body wall of a patient while the trocar extends through the body wall of a patient, the support comprising:

an annular expandable member for extending around the trocar, said annular expandable member being movable in an expansion movement from a collapsed condition radially outwardly of the trocar to a predetermined size;

an annular abutment collar arranged to be received on the trocar at a required position thereon;

the annular abutment collar being adjustable longitudinally of the trocar so as to be located at a selected position;

a releasable clamping member on the annular abutment collar for locating the annular abutment collar on the trocar at the selected position;

said annular expandable member being arranged while in said collapsed condition to be inserted through an incision in the body wall and expanded when inserted to engage an inside surface of the body wall;

wherein the annular expandable member comprises an elastomeric sleeve portion having an inner surface arranged to engage onto the trocar;

and wherein there is provided an insert sleeve portion on the annular abutment collar engageable into a hollow interior of the elastomeric sleeve portion for engaging the inner surface and the holding the inner surface open for passage of the trocar.

According to another aspect of the invention, which can be used independently or in combination with any of the above, there is provided a trocar support apparatus for use with a trocar separate from the apparatus for maintaining the trocar in fixed position in a body wall of a patient while the trocar extends through the body wall of a patient, the support comprising:

an annular expandable member for extending around the trocar, said annular expandable member being movable in an expansion movement from a collapsed condition radially outwardly of the trocar to a predetermined size;

an annular abutment collar arranged to be received on the trocar at a required position thereon;

the annular abutment collar being adjustable longitudinally of the trocar so as to be located at a selected position;

a releasable clamping member on the annular abutment collar for locating the annular abutment collar on the trocar at the selected position;

said annular expandable member being arranged while in said collapsed condition to be inserted through an incision in the body wall and expanded when inserted to engage an inside surface of the body wall;

a connecting component mounted on the annular abutment collar for engaging a portion of the annular expandable member to engage and hold the annular expandable member in engagement with the annular abutment collar for common insertion of the trocar therethrough to a required position of the annular expandable member on the trocar;

and a release member operable to release the connecting component to effect release of the annular expandable member from the annular abutment collar so that when released the annular abutment collar is movable longitudinally relative to the annular expandable member such that the annular abutment collar is moved to a position to hold the body wall between the annular abutment collar and the annular expandable member.

According to another aspect of the invention, which can be used independently or in combination with any of the above, there is provided a trocar support apparatus for use with a trocar separate from the apparatus for maintaining the trocar in fixed position in a body wall of a patient while the trocar extends through the body wall of a patient, the support comprising:

an annular expandable member for extending around the trocar, said annular expandable member being movable in an expansion movement from a collapsed condition radially outwardly of the trocar to a predetermined size;

an annular abutment collar arranged to be received on the trocar at a required position thereon;

the annular abutment collar being adjustable longitudinally of the trocar so as to be located at a selected position;

a releasable clamping member on the annular abutment collar for locating the annular abutment collar on the trocar at the selected position;

said annular expandable member being arranged while in said collapsed condition to be inserted through an incision in the body wall and expanded when inserted to engage an inside surface of the body wall;

wherein the manually operable device comprises a pair of members locating an inflation fluid containing member therebetween;

and a manually operable compression device for squeezing one member toward the other member for expelling the inflation fluid from the fluid containing member;

wherein the fluid containing member can be opened to enable the entry of sterilizing fluid and closed to effect the expulsion of the inflation fluid.

In one optional arrangement the fluid containing member is opened by a valve.

In another optional arrangement the fluid containing member is movable to a position where a chamber defined therebetween is opened to allow the entry of the sterilization fluid and then is closed to enclose a volume of the inflation fluid.

According to another aspect of the invention there is provided a trocar support apparatus for use with a trocar separate from the apparatus for maintaining the trocar in fixed position in a body wall of a patient while the trocar extends through the body wall of a patient, the support comprising:

an annular expandable member for extending around the trocar, said annular expandable member being movable in an expansion movement from a collapsed condition radially outwardly of the trocar to a predetermined size;

an annular abutment collar arranged to be received on the trocar at a required position thereon;

the annular abutment collar being adjustable longitudinally of the trocar so as to be located at a selected position;

a releasable clamping member on the annular abutment collar for locating the annular abutment collar on the trocar at the selected position;

said annular expandable member being arranged while in said collapsed condition to be inserted through an incision in the body wall and expanded when inserted to engage an inside surface of the body wall;

wherein the manually operable device comprises a pair of members locating an inflation fluid containing member therebetween;

the members including a manually engageable projection extending generally radially outwardly from the annular abutment collar;

and a manually operable compression device for rotating one member around the axis of the trocar toward of the other member for expelling the inflation fluid from the fluid containing member.

The following defined optional features can be used independently of one another with any of the above independent aspects of the intention described herein.

In accordance with one important independent optional feature of the invention, one of the annular members comprises a cylinder and the other of the annular members comprises a piston defining a chamber in the cylinder so that the movement in the axial direction causes the chamber to be reduced in volume expelling the fluid therefrom.

In accordance with one important independent optional feature of the invention, the cylinder and the piston can be moved to a position allowing entry of a sterilizing fluid material from the exterior to enable the chamber to be properly sterilized.

In accordance with one important independent optional feature of the invention, the manually operable compression device comprises a screw thread interconnecting the annular members so that rotation of one around the axis causes said relative axial movement.

In accordance with one important independent optional feature of the invention, the screw thread is on an outside surface of one of the annular members.

In accordance with one important independent optional feature of the invention, the manually operable compression device includes a latch for holding the annular members in fixed position after a volume of fluid is supplied.

In accordance with one important independent optional feature of the invention, the annular members are moved by squeezing together two abutments projecting from an exterior of each of the annular members where at least one of the abutments is rotatable around the axis.

In accordance with one important independent optional feature of the invention, there is provided a latch extending between the abutments for holding the abutments in fixed position after the fluid is supplied.

In accordance with one important independent optional feature of the invention, there is provided a spring which rotates the annular members in a return direction to a retracted position to deflate the expandable member.

In accordance with one important independent optional feature of the invention, the spring is located between the annular members and is wound around the trocar.

In accordance with one important independent optional feature of the invention, there is provided a connecting component mounted on the annular abutment collar for engaging a portion of the annular expandable member to engage and hold the annular expandable member in engagement with the annular abutment collar for common insertion of the trocar therethrough to a required position of the annular expandable member on the trocar and a release member operable to release the connecting component to effect release of the annular expandable member from the annular abutment collar so that when released the annular abutment collar is movable longitudinally relative to the annular expandable member such that the annular abutment collar is moved to a position to hold the body wall between the annular abutment collar and the annular expandable member.

In accordance with one important independent optional feature of the invention, the surface of the connecting component surrounds the trocar so that a portion of the annular expandable member projects axially into the interior of the surface.

In accordance with one important independent optional feature of the invention, the connecting component comprises a ring on the annular expandable member which is held by a sliding plate on the annular abutment collar with an opening in the plate to hold and release the ring.

In accordance with one important independent optional feature of the invention, the annular expandable member includes a sleeve slightly bigger than the trocar with an internal peripheral rib which engages over a rib on the trocar to lock the annular expandable member in place.

In accordance with one important independent optional feature of the invention, the annular expandable member is inflatable by a fluid. However other techniques for expansion of the expandable member can be used.

In accordance with one important independent optional feature of the invention, the manually operable device is mounted on the annular abutment collar. Other mounting arrangements can however be used.

In accordance with one important independent optional feature of the invention, the manually operable device comprises a pair of discs with a fluid containing member such as a balloon, located therebetween, the discs and the fluid containing member surrounding a central opening for passage therethrough of the trocar.

In accordance with one important independent optional feature of the invention, there is provided a manually operable compression device such as a threaded member rotatable on the device for squeezing one of the discs toward of the other discs for compression of the fluid containing member.

In accordance with one important independent optional feature of the invention, the coupling arrangement includes an insert sleeve portion engageable into a hollow interior of the elastomeric sleeve portion for engaging the inner surface and the holding the inner surface open for passage of the trocar. Preferably the insert sleeve portion is tapered so as to hold the elastomeric sleeve portion in a frustoconical portion at the end edge of the elastomeric sleeve portion. This allows the trocar to slide through sleeve portion and to be guided into the leading edge of the elastomeric sleeve to reduce longitudinal forces on the elastomeric sleeve which could otherwise cause it to move longitudinally with the trocar.

In accordance with one important independent optional feature of the invention, the coupling arrangement includes a peripheral engagement member for clamping a portion of the elastomeric sleeve portion against the insert sleeve portion. This acts to hold the elastomeric sleeve clamped in position with the annular abutment collar until it is released to allow the collar to slide away from the elastomeric sleeve for the insertion process in the body cavity of the patient.

In accordance with one important independent optional feature of the invention, the peripheral engagement member is releasable from the insert sleeve portion and the elastomeric sleeve portion by the manually operable release member. Preferably the release member is movable axially to release the peripheral engagement member, for example by rotation on a screw thread.

In accordance with one important independent optional feature of the invention, an edge portion of the annular expandable member or elastomeric member is clamped between an inner insert sleeve portion and an outer peripheral engagement member to hold the edge portion clamped to the annular abutment collar.

In accordance with one important independent optional feature of the invention, the releasable clamping member on the annular abutment collar comprises a disk member having a central opening for surrounding the trocar, the central opening having an edge portion spring biased in a direction axially toward the trocar for engaging the trocar, and the disk member having a manually engageable portion exposed at one side of the annular abutment collar for pressing the disk member in a direction of the central opening axially away from the trocar against the spring bias.

In the case where the expandable member is expanded by fluid, preferably there is provided a tubular conduit which connects the source of fluid to the annular expandable member wrapped helically around the trocar.

BRIEF DESCRIPTION OF THE DRAWINGS

One embodiment of the invention will now be described in conjunction with the accompanying drawings in which:

FIG. 2 is a first side elevational view of the embodiment of FIG. 1.

FIG. 3 is a second side elevational view of the embodiment of FIG. 1.

DETAILED DESCRIPTION

Figure 4:
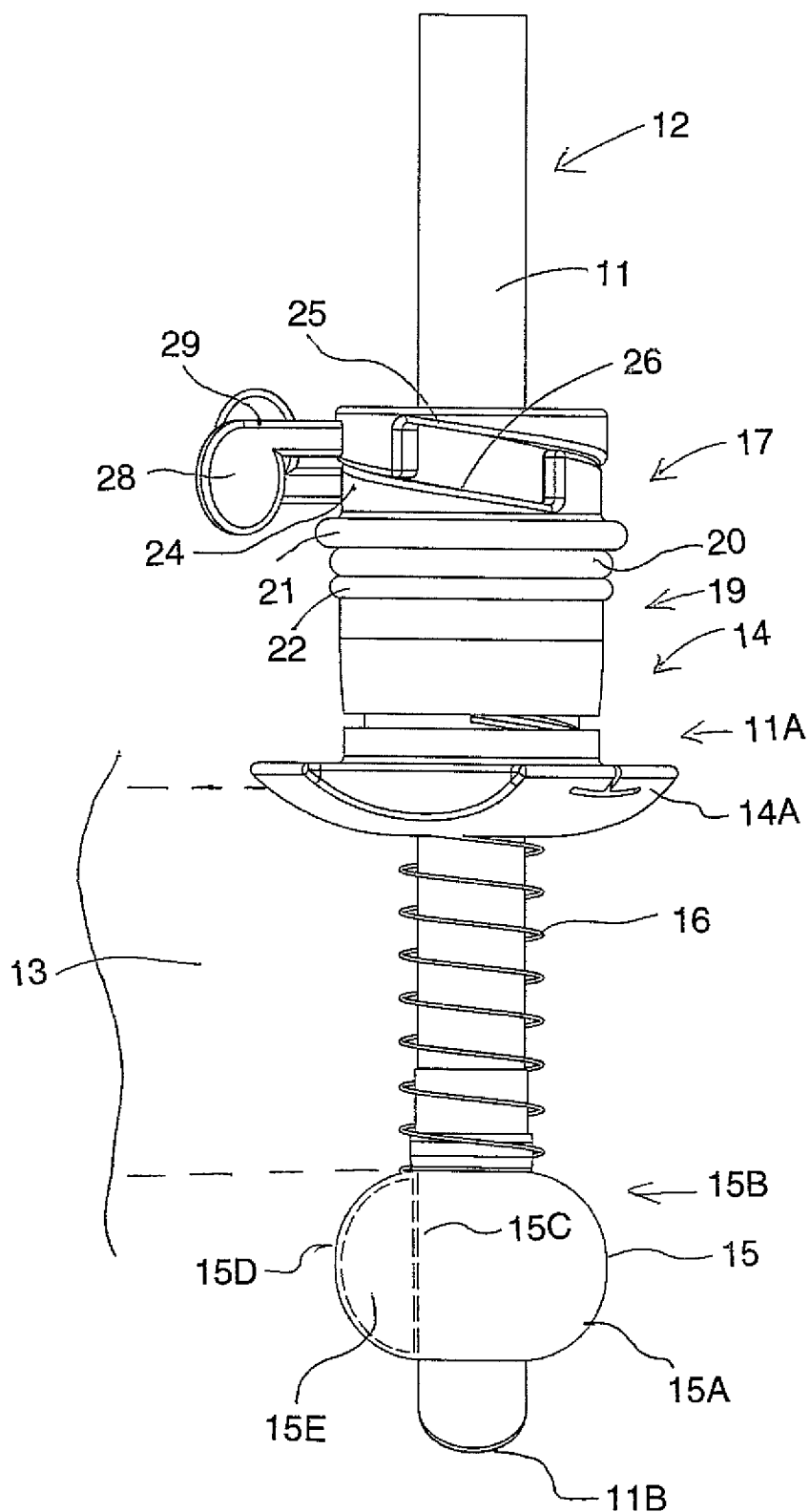
FIG. 4 is a third side elevational view of the embodiment of FIG. 1 shown in an expanded position.

In FIGS. 1 to 9 is provided a trocar support 10 for attachment to a trocar 12 to support a sleeve 11 of the trocar 12 while the sleeve 11 penetrates through a body wall 13 of a patient as shown schematically in the FIG. 4.

The support 10 comprises an abutment member 14 shaped to be received on an outer surface of the trocar sleeve. The abutment member forms a collar 14A surrounding the sleeve with a manually operable clamp 14B for releasable connection to the sleeve 11 so as to be adjustable longitudinally of the trocar sleeve 11 so as to be located at a selected position 11A as shown in FIG. 4.

The support 10 includes an inflatable collar 15 for mounting on the trocar sleeve 11 at a required position 15B spaced from the abutment member 14 at the position 11A. The inflatable collar can be inflated by a source of fluid, typically air or other gas, from a pump 17 to a predetermined size through a supply tube 16.

Figure 1:
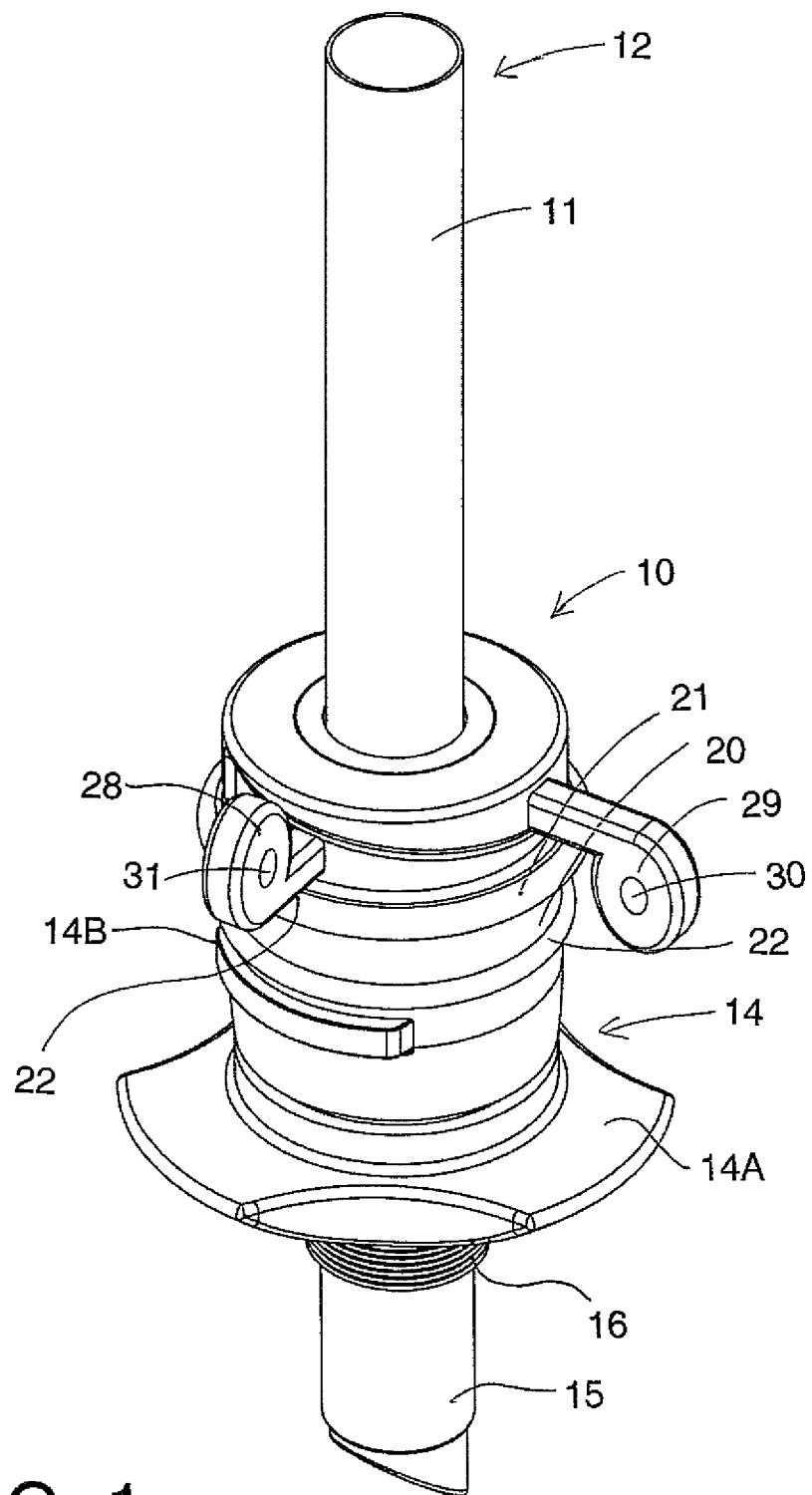
FIG. 1 is an isometric view from the top and one side of a trocar support according to the present invention.

As shown in FIG. 1, the inflatable collar while deflated can be inserted on the trocar sleeve through an incision in the body wall and can be inflated from the pump 17 through the tube 16 when inserted to the inflated condition shown in FIG. 4 at 15A to engage an inside surface of the body wall 13. The abutment member can be moved to a position 11A to hold the body wall 13 between the abutment member 14 and the inflatable collar 15.

The source of fluid provided by the pump 17 is located on the trocar support and particularly the abutment member 14 so as to be carried thereby.

The source of fluid therefore is a pump mechanism forming a part of the trocar support and operable by hand. The source of fluid 17 provides a fixed volume allowing inflation of the collar 15 only to a fixed size.

The tube 16 is of a circular cross-section or in some cases of a flattened cross-section so as to lie flat against the sleeve of the trocar and is wrapped helically around the sleeve of the trocar. Thus it can lie in compressed side by side turns as shown in the initial position in FIG. 1 and can extend axially as shown in FIG. 4.

As shown in FIG. 1, the inflatable collar 15 and the abutment member 14 form a common collar portion 10 which can be engaged onto the trocar sleeve 11 and moved axially therealong from the lower insertion end to a required position along the length of the trocar sleeve. In order to hold the assembly rigid and intact for insertion onto the trocar, there is provided a connection system 19.

The abutment member 14 can move axially along the trocar sleeve from the inflatable collar 15 when the latter has reached its required axial location 15B with the tube 16 being extended along the trocar sleeve as the abutment member moves away from the inflatable collar.

As described hereinafter the connection system 19 includes a component to hold the inflatable collar 15 against axial movement at the required location 15B on the trocar sleeve. This device can operate using many different techniques as described below, so as to ensure that the collar 15 remains at the required location until the inflation secures it more effectively.

Additional attention may be required in regard to some constructions to ensure that the lower inflatable collar remains in place after application of the device to the trocar and while the trocar is inserted into an incision in the body wall of the patient.

This arrangement is more convenient for a surgeon to insert and remove from the patient than the conventional arrangements of this type where the protrusions are actually a course thread and the trocar sleeve must be threaded into and out of the incision and fascia. The twisting action while inserting or removing a conventional threaded trocar can traumatize the fascia. The described arrangement is intended to be engaged within the fascia itself after it is inserted, thus avoiding potential damage to the fascia from the twisting action.

Other conventional arrangements, use ribs so as to attempt to reduce the possibility that the trocar is pulled from the incision. However these arrangements are also ineffective in that ribs may hold the trocar more effectively but in the event that the ribs are pulled through the incision, further and more damaging trauma may occur to the incision. Also the incision stretches over time and so the ribs become ineffective.

The arrangement of the present invention is therefore provided so as to form specific stop members on the inside and outside of the incision to prevent the trocar from migration. This arrangement where the device is separate from the trocar and is applied onto the trocar prior to its use allows the device to be used with different forms of trocar and different dimensions of trocar as a separate disposable item. The ability to adjust the positions of the inflatable collar on the trocar and also the slidable collar allows the surgeon to select the longitudinal position of the trocar relative to the incision. The present arrangement provides for the first time an effective separate support tool for use with different trocars.

In the present arrangement the inflation is effected by an inflatable manual pump of the type previous described which is carried on a collar part of the trocar itself. This controls the amount of fluid applied and obviates the need for separate fluid source.

The trocar support apparatus 10 is therefore used with the trocar 12 where the apparatus 10 is a separate component from the trocar itself enabling the apparatus to be disposable independently of the trocar so the trocar may be a reusable item. The support apparatus acts to maintain the trocar in the fixed position in the body wall of the patient while the trocar extends through the body wall of the patient.

The apparatus therefore includes the expandable member 15 which comprises a body for surrounding the trocar including an inner wall 15C and an outer wall 15D defining a chamber 15E therebetween. The inner wall 15C is arranged to closely surround the sleeve of the trocar in a friction fit so as to remain in place when installed at the required location 15B. The inflation of the fluid into the chamber 15E assist in maintaining the inner wall 15C in the fixed position. This position can either be directly at the end of the trocar sleeve or can be a selected position spaced along the trocar sleeve as chosen by the surgeon depending upon the intended position of the end 11B of the trocar.

The tube 16 which leads from the source of fluid to the inflatable member is formed with a sealed connection into the chamber 15E and extends in the helical manner around the trocar to the source.

The annular abutment collar 14 is also arranged to be received on the trocar and the required position and can be fixed in place by the manually operable button 14B. The button 14B acts as a releasable clamping member for engaging the sleeve or 11 at the required position.

Figure 5:
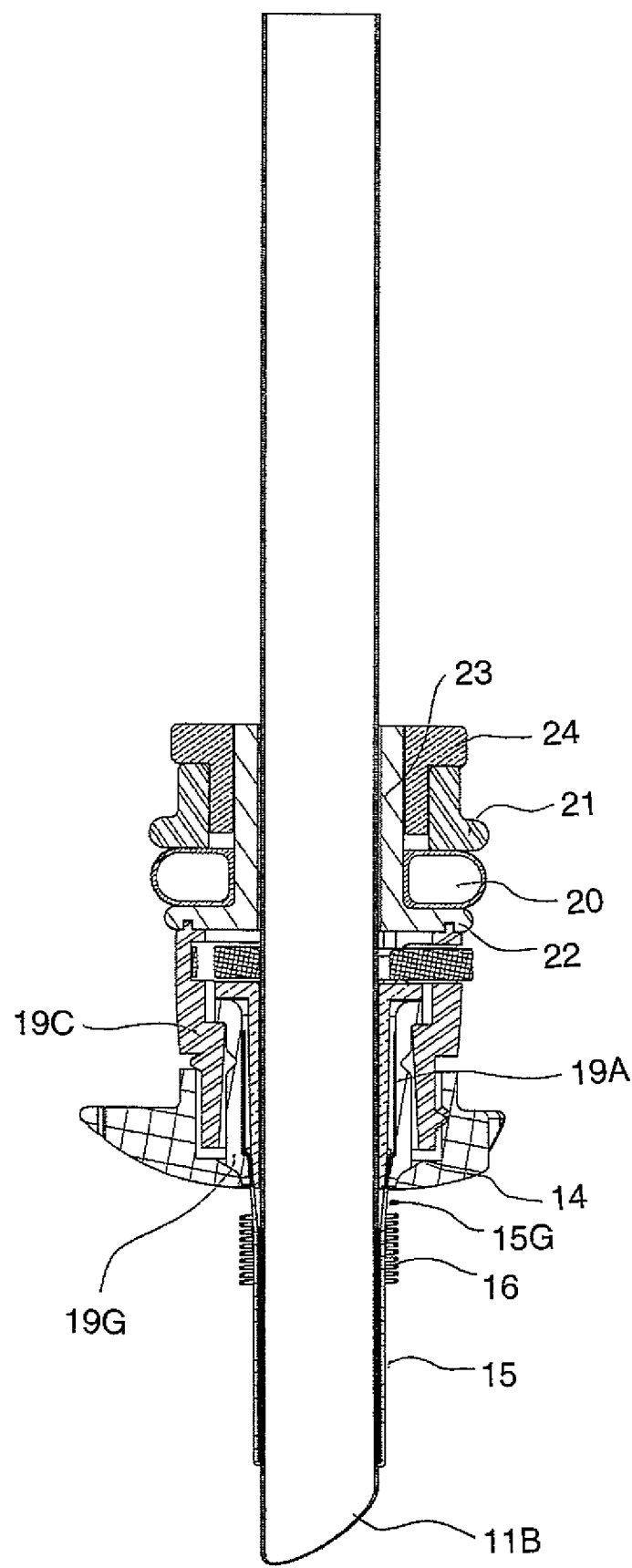
FIG. 5 is a first longitudinal cross-sectional view of the embodiment of FIG. 1 showing the expandable member and the collar in a position latched together.
Figure 6:
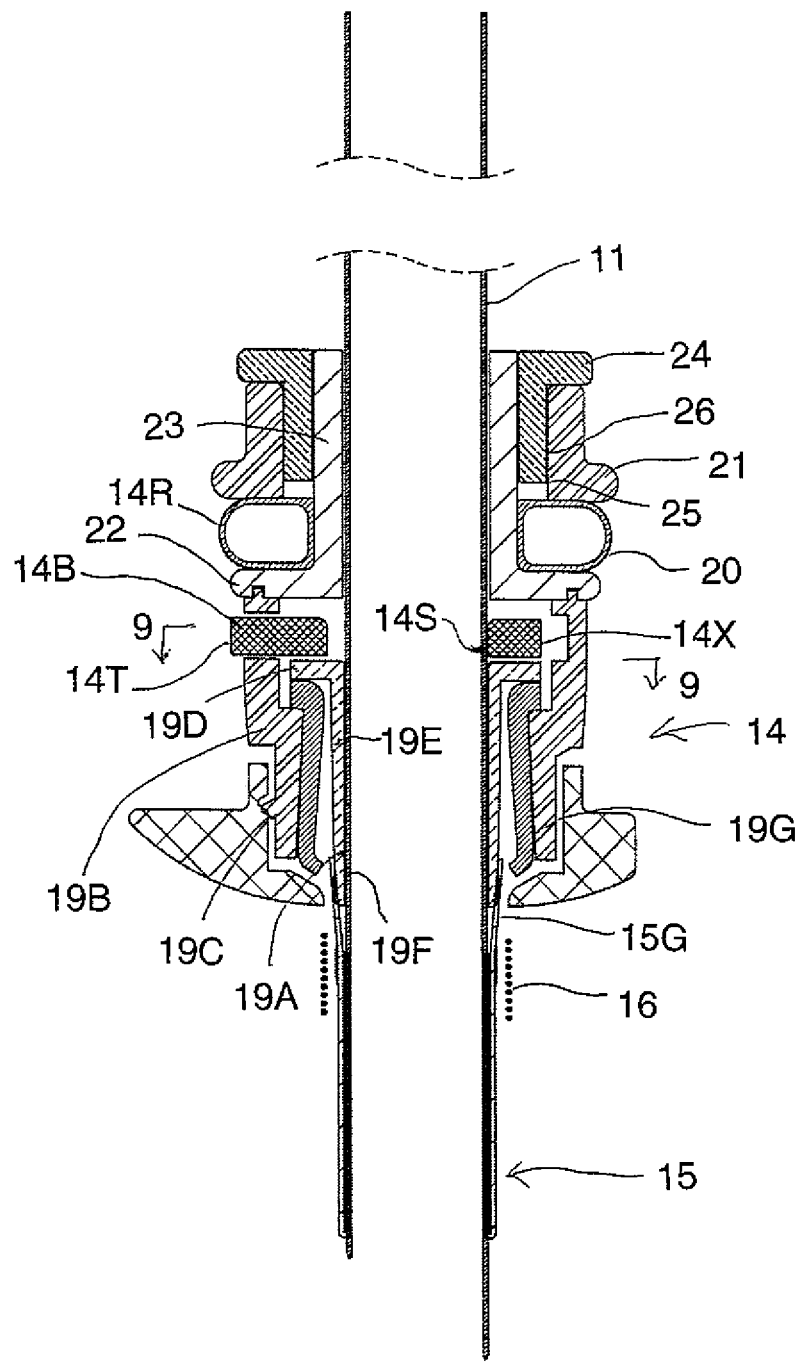
FIG. 6 is a second longitudinal cross-sectional view of the embodiment of FIG. 1.
Figure 8:
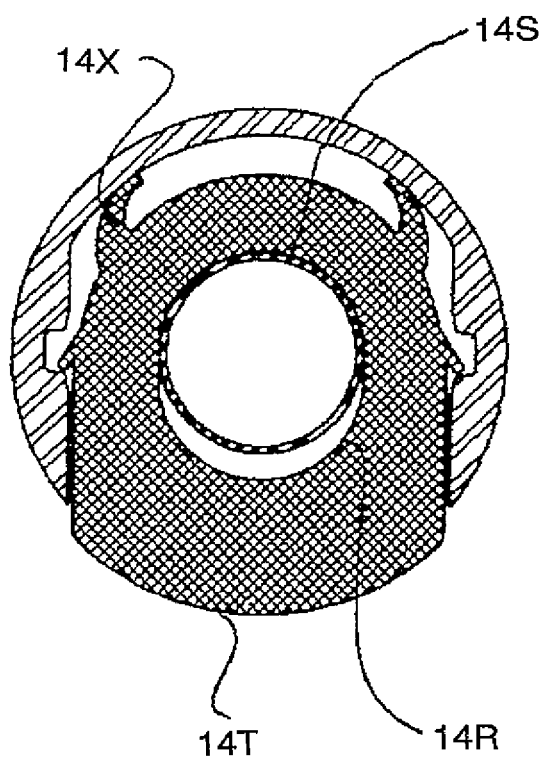
FIG. 8 is a cross-sectional view along the lines 9-9 of FIG. 6. In the drawings like characters of reference indicate corresponding parts in the different figures.

The coupling arrangement 19 includes a connecting assembly defined by a first piece 19A and the second piece 19B as best shown in FIGS. 5, 6 and 8. These pieces act to hold the annular expandable member 15 as a common component with the annular abutment collar 14 for common insertion of the trocar through these components to the required position. The two pieces are releasable by a release component 19C to effect release of the annular expandable member 15 from the collar 14 so that when released the collar 14 is longitudinally movable relative to the expandable member 15 so that the collar can be moved to the required position adjacent to the exterior of the body wall to squeeze the body wall between the collar and the expandable member to hold the device and therefore the trocar in place.

As best shown in FIGS. 2 and 3, the source of fluid connected to the upper end of the tube 16 comprises a disc-shaped bladder 20 surrounding the trocar 11 and compressible between a pair of annular member defined by two operating discs 21 and 22. The disc 22 has the bladder 20 attached to the surface of the disc 22 facing the disc 21 so as to be carried thereby. The disc 22 forms an integral component with a collar or sleeve 23 which surrounds the trocar 11. The disc 21 is carried in an upper collar 24 which can slide along the outer surface of the sleeve 23 in a sliding action in which the disc 21 approaches the disc 22. Therefore sliding action of the disc 21 downwardly toward the disc 22 causes the annular bladder 20 to be compressed to expel the full amount of fluid within the bladder. This sliding action is carried out by a threaded arrangement formed by ramp surfaces 25, 26 on the collar 24 and on the rear surface of the disc 21. A spring 27 is located between the ramp surfaces 25 and 26 and acts to bias the discs 21 and 22 apart in to an expanded position of the bladder 20. Movement of the discs 21 and 22 to a compressed position of the bladder 20 is carried out by a pair of levers 28 and 29 which are squeezed together manually so as to rotate the collar 24 relative to the disc 21 so that the ramp surfaces cause the longitudinal movement of the disc 21 toward the disc 22.

Each of the levers 28, 29 includes a manually operable finger pad allowing the finger and thumb of the user to squeeze the levers together. A latching arrangement schematically illustrated in FIG. 1 at 30, 31 is provided to hold the finger pads together in a locked position when the levers are moved to the squeezed up position expelling the fluid from the bladder 20. The latch 30, 31 is operated only when the levers are fully squeezed so that if the levers do not reach the fully squeezed position then that no latching occurs and the spring 27 acts to return the levers to the initial position thus re-filling the bladder 20 and retracting the fluid from the expandable member 15. The device therefore requires that the user operate the levers only to the fully squeezed position and prevents any possible situation where the member 15 is only partly expanded. The latch 30, 31 is also arranged to release in the situation where the finger pads are pushed together at a time after the latched expansion has been completed. Thus the user in operation causes the expansion of the member 15 and releases the finger pads in the latched position. At a later time when it is required to deflate the member 15 after the procedure is completed, a further compression of the finger pads causes the latch 30, 31 to be released so the spring 27 causes the deflation of the member 15.

The discs 22 and 21 together with the bladder 20 have a central circular opening 32 for passage of the trocar 11.

Figure 7:
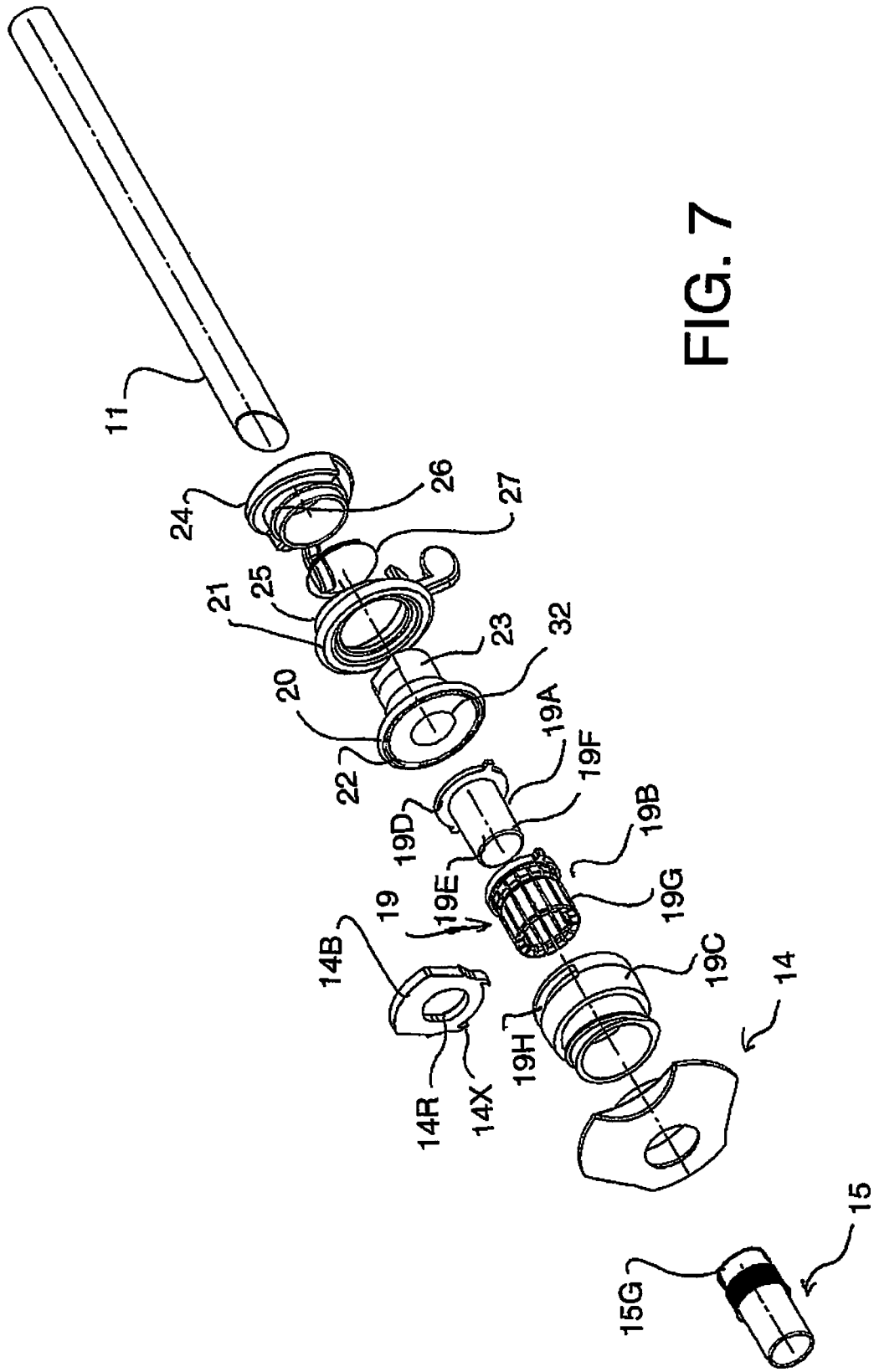
FIG. 7 is an exploded view of the embodiment of FIG. 1.

The coupling arrangement 19 is best shown in FIGS. 5, 6 and 7. This includes the component 19A which has a collar 19D and a sleeve 19E. The sleeve 19E is tapered at an end 19F so as to form an end portion which can be inserted into a frustoconical section 15G of the inflatable member 15. The section 15G is located at the end of the member 15 adjacent the sleeve 19E and its end portion 19F so that the end portion 19F holds the section 15G open for passage of the trocar through the channel 32 and through the sleeve 19E into the member 15. In this way the upper end of the member 15 is prevented from being pushed downwardly by the end 11B of the trocar. The section 15G of the inflatable member is maintained in a frustoconical position by the tapered section 19F and reverts to a cylindrical position surrounding the trocar when the second 19F is removed due to the elastic nature of the inflatable member.

In order to prevent the frictional engagement between the outside surface of the trocar on the inside surface of the member 15 from tending to push the member 15 downwardly before its selected position, the member 19B is used to pinch the outside surface of the portion 15G onto the tapered end 19F, In order to do this, the member 19B includes a plurality of fingers 19G with end tips which engage the outside surface of the portion 19F when the fingers 19G are squeezed together. In initial assembly of the construction, the fingers 19G are squeezed together by the coupling 19C on the collar 14. However rotation of the coupling 19C causes a threaded ramp 19H to move the coupling 19C axially along the fingers 19G so as to allow the fingers to move outwardly away from the portion 15G. This operation can be seen best by comparing FIGS. 5 and 6 where in FIG. 5 the fingers 19G are compressed inwardly to squeeze against the portion 15G. In FIG. 6 the coupling 19C has moved axially allowing the spring in the fingers 19G to cause the fingers to move outwardly away from the portion 15G. In this way the portion 15G is held pinched during the insertion of the trocar through the device and then it is released at the required position selected by the user by rotating the collar 14 and the coupling 19C so that the portion 15G is allowed to slide off the tapered end 19F. The frictional contact between the inside surface of the member 15 and the trocar allows the member 15 to be pulled off the device and placed onto the trocar while the remaining part of the device, move axially away from the member 15. This movement causes the tube 16 to expand along the length of the trocar so that it extends from the inflatable member 15 to the expansion bladder 20.

Figure 9:
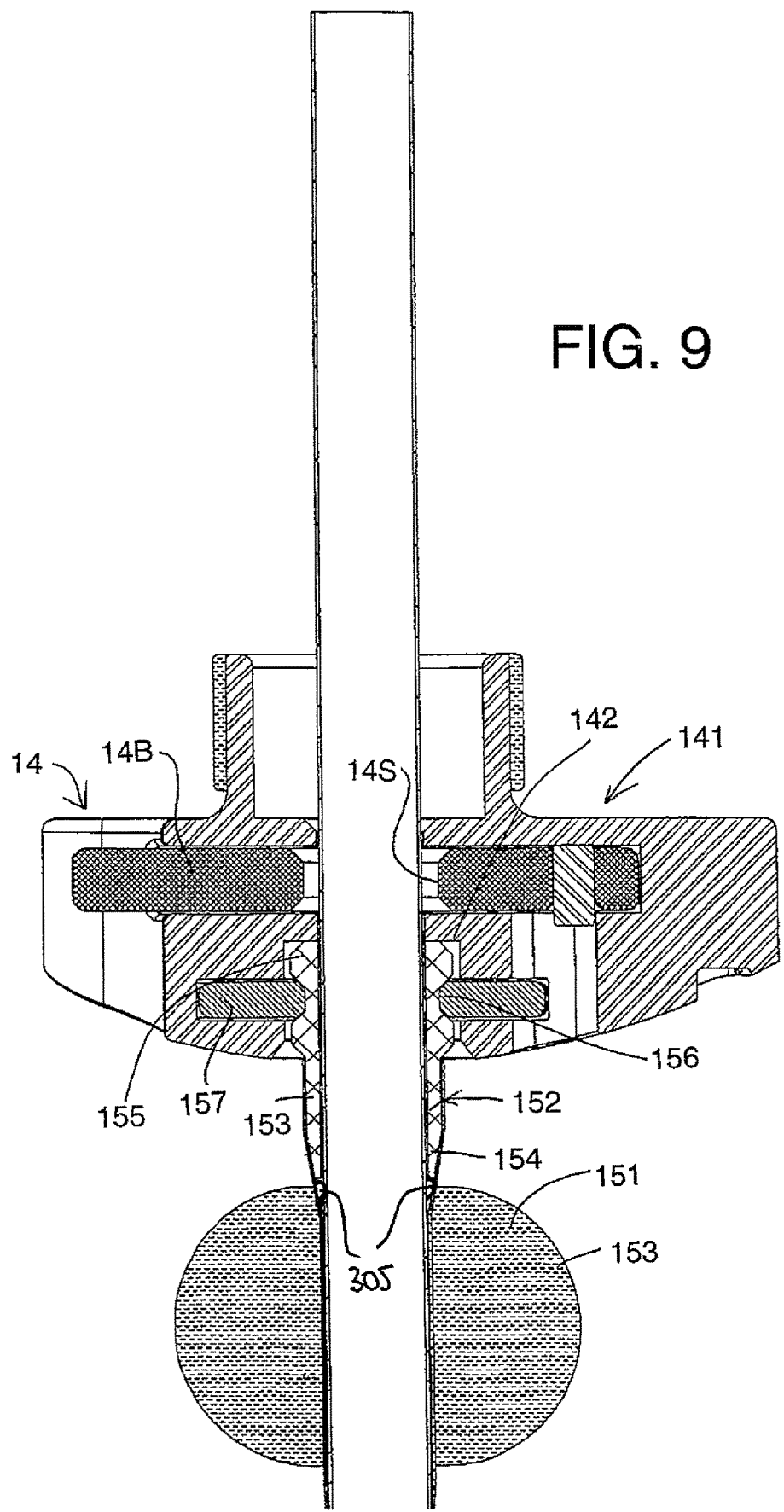
FIG. 9 is a longitudinal cross-sectional view of a second embodiment of the trocar support according to the present invention.

As shown in FIGS. 6, 9 and 8, the annular abutment member 14 surrounds the opening 32 to allow the passage of the trocar. A manually releasable clamping member 14B is provided on the abutment member 14 for clamping onto the outside surface of the trocar. The clamping member 14B comprises a flat disk with a central opening 14R which surrounds the trocar. One side edge 14S of the opening 14R pinches against the outside surface of the trocar as shown in FIG. 6. However pressure against an end portion or button 14T of the member 14B acts to push the disc so that the edge 14S is moved away from the outside surface of the trocar. The opening 14R is thus non-circular so that when depressed by the button 14T is moved away from the trocar. A spring arrangement 14X is provided at the back of the disc opposite the button 14T so as to push the disc into engagement between the edge 14S and the trocar except when the button 14T is depressed.

The arrangement here and therefore provides a single unit where the inflatable member 15 and the annular collar 14 are connected together during the insertion of the trocar. The connection between them is divided by the components themselves rather than any additional removable components. Simple rotation of the collar 14 allows the separation of the collar from the inflatable member to occur at a required position of the inflatable member selected by the user. When the inflatable member is in position on the trocar, the collar can be moved away from the inflatable member sufficiently for the user to insert the trocar through the body wall of the patient so that the inflatable member is located inside the body wall allowing it to be inflated by compression of the bladder 20 through the tube 16, following which the collar 14 is moved up to a position outside the body wall of the patient to effect squeezing of the body wall sufficient to hold the trocar in place. Release of the inflation of the body after the operation is complete is carried out by releasing the latch 30, 31 which causes the inflatable member to deflate allowing the trocar to be simply pulled from the incision.

In FIG. 9 is shown an alternative arrangement which uses the same inflation system as described above for supplying fluid to the inflatable member 151. In this arrangement an alternative construction is provided for attaching the inflatable member 151 to the collar 141. In this arrangement the inflatable member 151 includes an upper portion generally indicated at 152 which extend upwardly beyond the inflatable portion indicated at 153. The upper portion 152 is all increased thickness and tapers downwardly at 154 to form the inner surface of the inflatable balloon 153. Above the tapered portion 154 is provided a sleeve 153 which extend upwardly and that is then shaped to form a collar portion 155 with a recess 156 surrounding the collar portion. A clamping ring 157 engages into the recess 156 to hold the collar portion 155 within a recess 142 of the collar 141. The clamping ring 157 is releasable by any suitable mechanical method such as sliding or rotation to move away from the recess 156 to release the inflatable member 151 from its clamp position in engagement with the collar 141. The device operates therefore in the same manner as described in that the inflatable member is held clamped to the collar 141 while the trocar is inserted through the collar 141 and through the portion 152 of the inflatable member 151 until the inflatable member 153 reaches the required position. At this point the member 157 is operated to release the inflatable member and to allow the collar 141 to be moved away.

Figure 10:
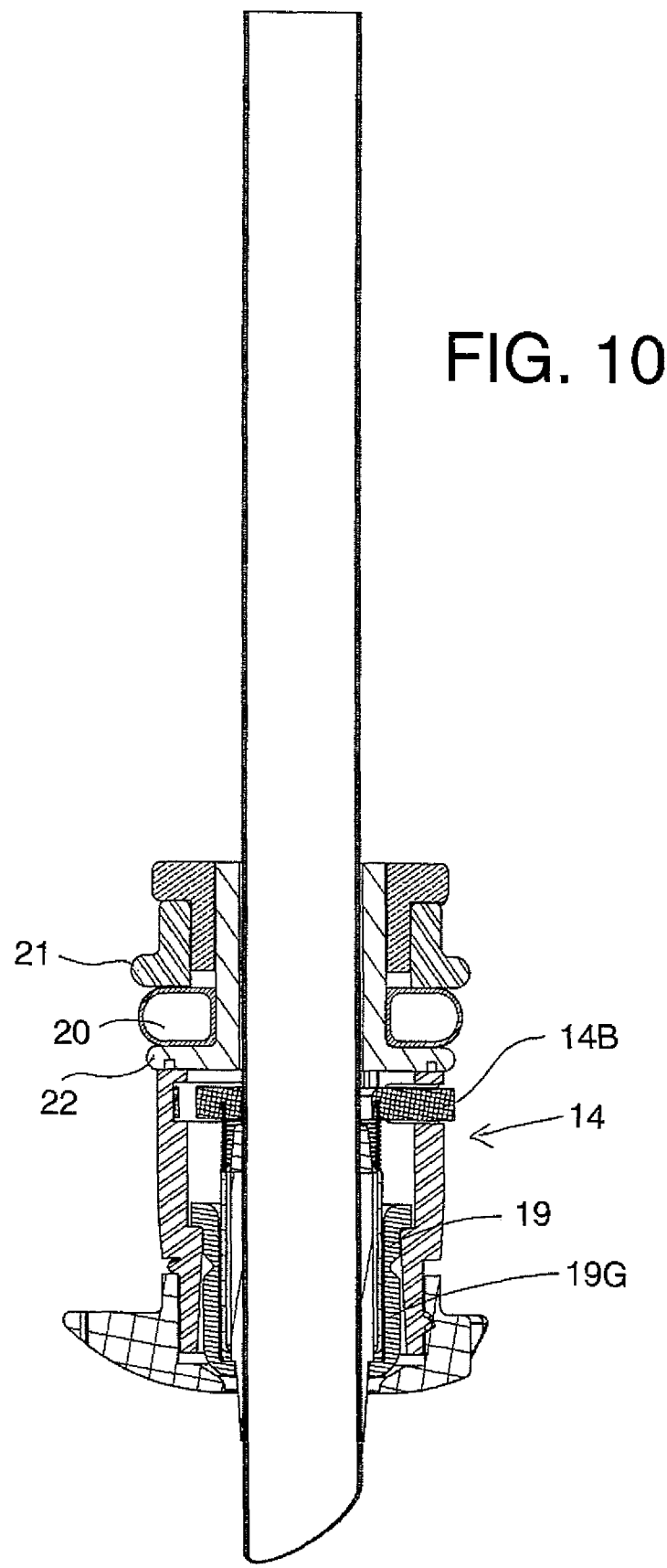
FIG. 10 is a longitudinal cross-sectional view of a third embodiment of the trocar support according to the present invention.
Figure 11:
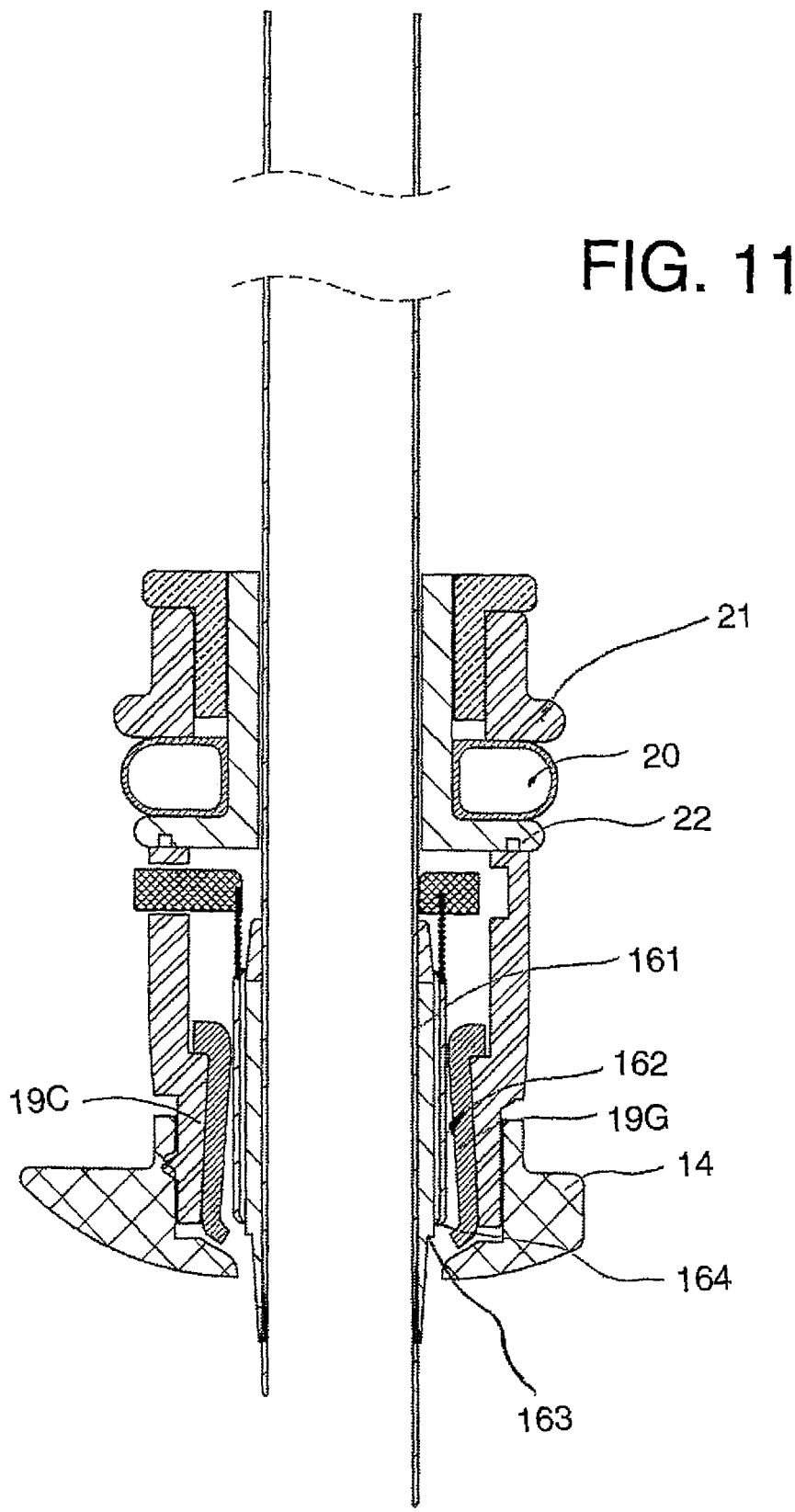
FIG. 11 is a longitudinal cross-sectional view of the embodiment of FIG. 10.

Turning now to FIGS. 10 and 11, there is shown a further arrangement which uses the same components as described above in relation to FIG. 6 including the fingers 19G. However in this embodiment instead of merely pinching the top edge of the balloon or inflatable member between the fingers on the conical section 19F, the fingers 19G cooperate with a bottom shoulder 163 of an inner wall 164 of the inflatable member 161. This inflation fluid is injected in this inflatable member 161 between the inner wall 163 and the outer inflatable portion 162 to effect the inflation when required. However the thickness of the inflatable member at the inner wall is sufficient to define the shoulder 163 which can be suitably grasped by the fingers 19G to hold the inflatable member 161 within the interior of the collar 14.

Thus in both of the embodiments of FIGS. 9, 10 and 11, inflatable member is of a more complex and thicker construction which may be disadvantageous in that the thicker wall must pass through the incision, but this thicker construction allows a more effective clamping action of the component of the collar 14 on to the inflatable member 15 to hold it better in place. In addition this arrangement may reduce the overall length of the system so as to avoid taking up excessive amount of the length of the shaft of the trocar which could interfere with the insertion into the incision.

Turning now to the embodiment of FIGS. 12 to 16, there is shown a trocar support apparatus 201 for use with a trocar T separate from the apparatus. The apparatus comprises an annular expandable member 203 for extending around the trocar which includes a balloon portion 204 expandable in an inflation movement from a collapsed condition radially outwardly of the trocar to a predetermined size for engaging the interior of the body of the patient as previously described.

The apparatus further includes an annular abutment collar 202 arranged to be received on the trocar at a required position thereon which is adjustable longitudinally of the trocar so as to be located at a selected position on the trocar to allow the insertion into the incision and then to clamp against the outside of the body as previously described.

The slidable collar 202 comprises a generally cylindrical body forming four sections 205 to 208 arranged in a row and coaxial around a hollow core through which the trocar passes.

The slidable collar 202 includes a releasable clamping member as section 207 of the annular abutment collar for locating the annular abutment collar on the trocar at the selected position when adjusted.

As described above, the expandable collar 203 is arranged while in its collapsed condition as shown to be inserted through an incision in the body wall and then expanded when inserted to engage an inside surface of the body wall.

The annular expandable collar is inflatable by a manually operable device providing a source of air in the form of a pump defined by a pair of members 205 and 206 mounted on the slidable collar 202. In particular the pair of members or sections 205 and 206, which are annular so as to surround a central opening 209 for passage therethrough of the trocar, define a fluid containing chamber 210 therebetween. The sections 205 and 206 each carry abutments 212 and 213 of a manually operable compression device for engagement by the finger and thumb of the user for squeezing the section 205 in an axial direction toward of the other section 206 for expelling fluid from the fluid containing chamber 210 through a helical duct 215 as previously described to the expandable collar 203, 201.

The section 206 forms an annular cylinder 227 having a cylindrical exterior wall 214 and a closed bottom wall 216 into which the duct 215 connects. The cylinder further includes an inner wall 217 with both the inner wall 217 and the outer wall 214 terminating at upper edges 218, 219.

The section 205 carries an internal annular piston 220 with a base 221, an outer wall 222 and an inner wall 223. The walls 222 and 223 each have an external channel 225 carrying sealing rings 226 for sliding movement on the inside surfaces of the cylinder. The piston 220 and the cylinder 227 define therebetween the chamber 210 in the cylinder so that the movement in the axial direction causes the chamber 210 to be reduced in volume expelling the fluid therefrom through a second opening defined by the duct 215. The channels and sealing rings can be replaced by a wiper seal arrangement (not shown) integrated into the outer wall of the piston.

The outer wall 214 of the cylinder carries a shallow screw thread 228 which connects with a cooperating recess 229 in a sleeve portion 230 of the section 205. Thus the section 205 includes an upper cap 231 and the depending sleeve 230 surrounding the outer wall of the cylinder defined by the section 206. The screw thread thus acts for interconnecting the annular members defined by the sections 205 and 206 so that rotation of one around the axis causes relative axial movement to force the piston into the cylinder.

The screw thread is arranged so that the cylinder 227 and the piston 220 can be moved to a position in which the seal 226 is moved to a position defining a first opening allowing entry of a sterilizing fluid material from the exterior to enable the chamber 210 to be properly sterilized. The device can thus use conventional sterilizing systems to pass cleaning fluid through the whole system including the chamber. Once the seals enter the cylinder, a fixed volume of air is defined in the chamber 210 which is then expelled as the section 205 is moved downwardly to provide that fixed volume to the inflatable collar to ensure inflation to a predetermined size.

Figure 12:
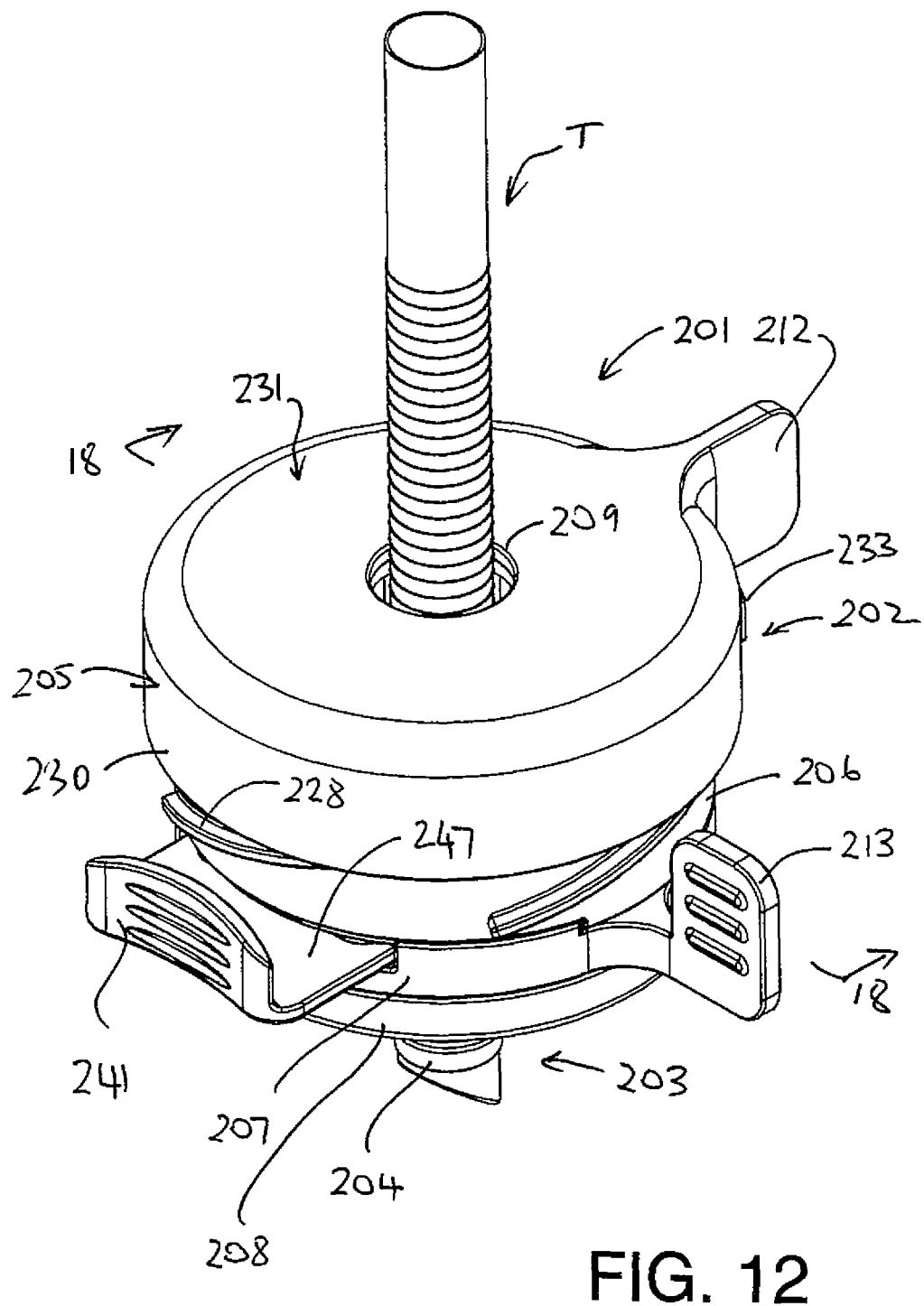
FIG. 12 is an isometric view from the top and one side of a trocar support according to a fourth embodiment of the present invention in a first position of the inflation system.
Figure 12A:
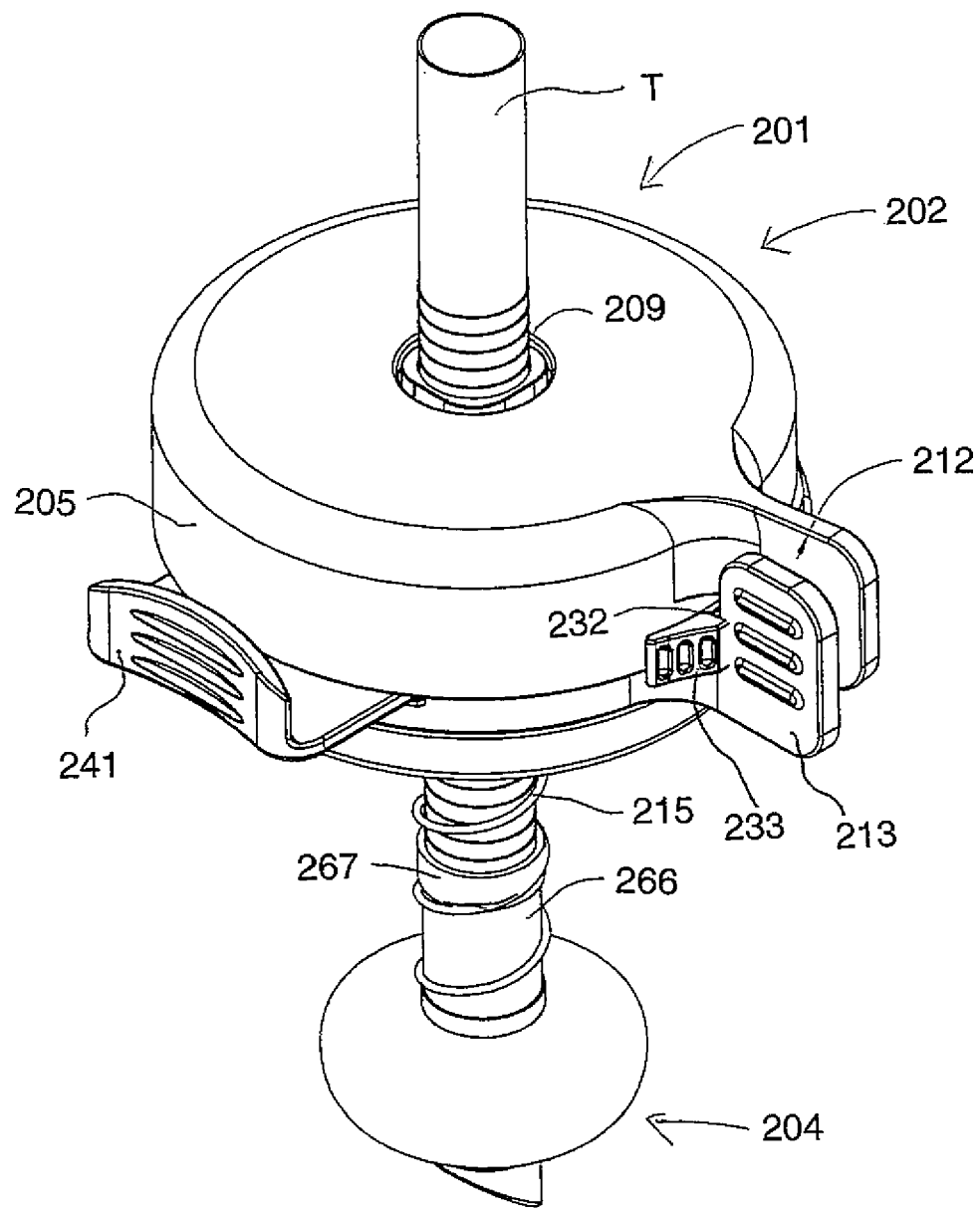
FIG. 12A is a view similar to that of FIG. 12 showing the inflation system in a final position of the inflation system.
Figure 13:
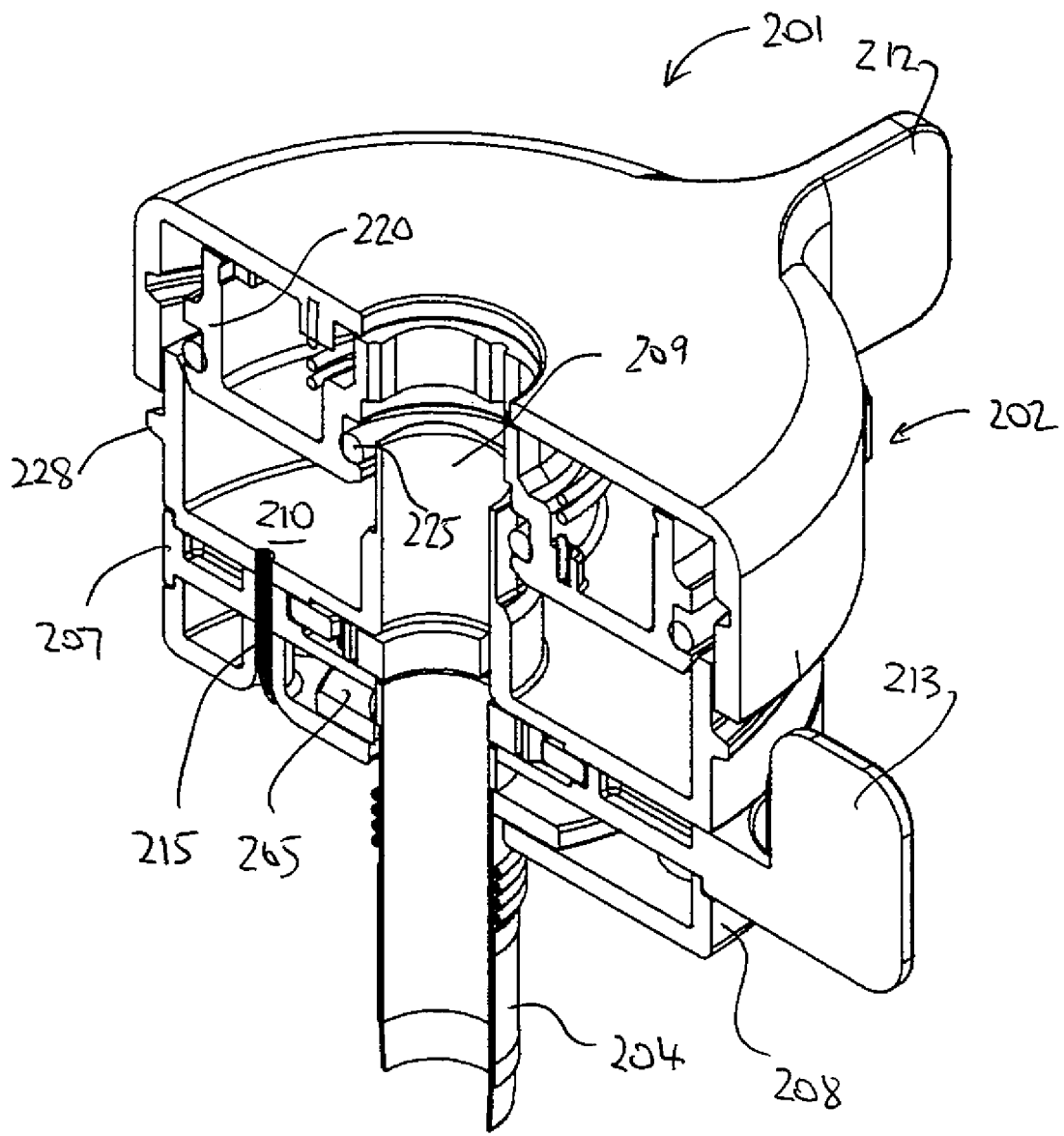
FIG. 13 is an isometric view partly in cross-sectional of the embodiment of FIG. 12.
Figure 14:
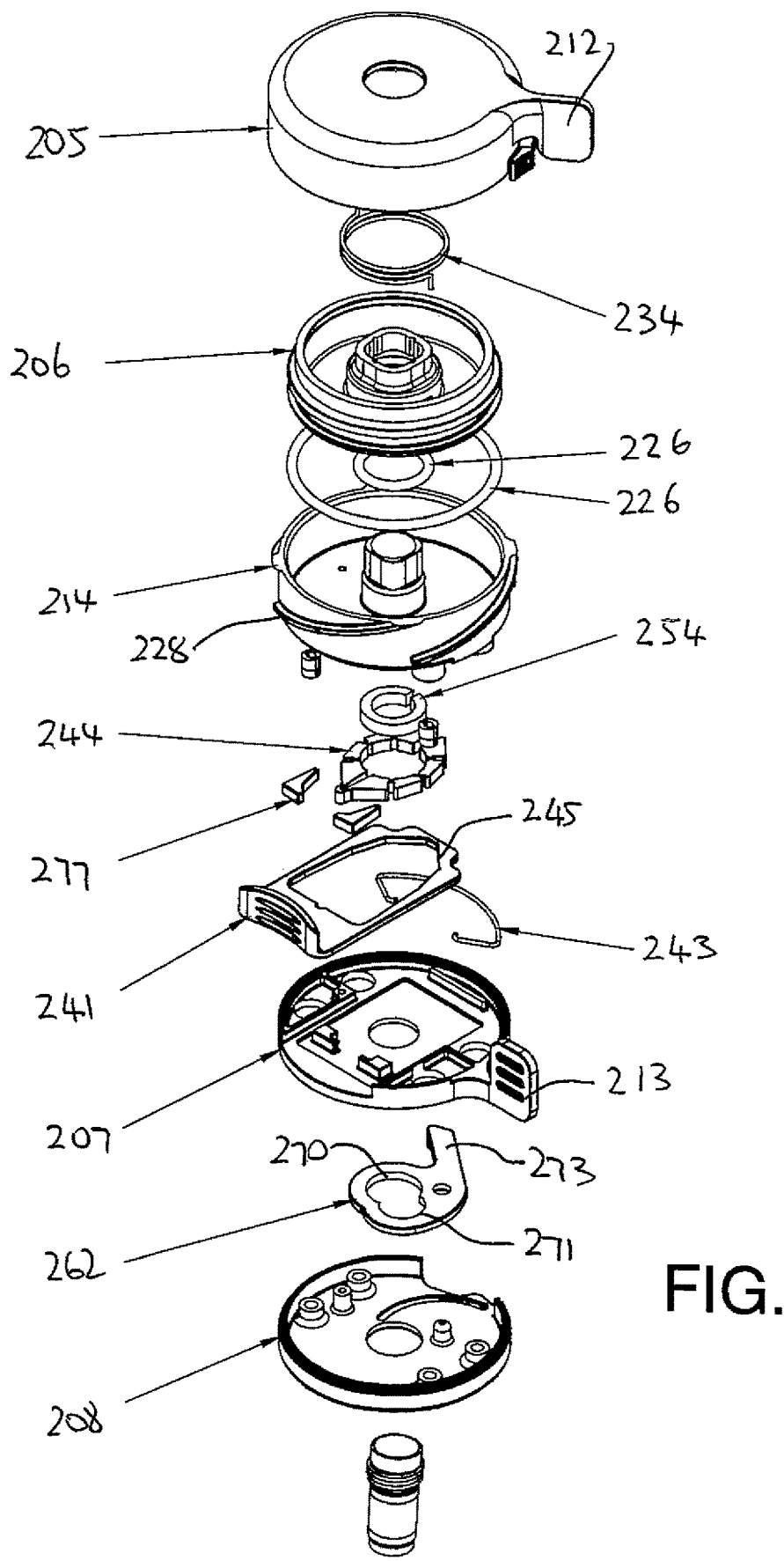
FIG. 14 is an exploded view of the embodiment of FIG. 12 showing the internal components.

The piston 220 on the section 205 is driven forwardly relative to the cylinder on the section 206 by squeezing together the two abutments 212 and 213 projecting radially outwardly from an exterior of each of the annular members. The piston itself does not rotate as it is held stationary relative to the cylinder as the outer cap 231 rotates and there is a bearing between these components. The finger and thumb abutments 212 and 213 start at an angle of the order of 40 degrees and are moved together by relative rotation around the axis of the trocar in the squeezing action until they are at or close to touching. The position shown, which is roughly at 120 degrees, shows the position in which the section 205 is moved to a release position for the sterilizing fluid to enter the cylinder around the head of the piston. A latch is defined by a latch finger 232 and a latch head 233 where the latch finger 232 is attached to the abutment 212 and extends inside the abutment 213 (FIG. 12A) and the includes a latch head 233 snaps behind the abutment 213 to hold the abutments in the closed position until the user releases the latch head from the latching position.

A coiled torsion spring 234 is wrapped around the center core 209 and located between the annular members is attached at one end 235 to the section 205 and at the other end 236 to the section 206. The spring is tightened as the section 205 is rotated to the latched position and acts, when the latch is released, to rotate the sections in a return direction to a retracted position shown in FIG. 12 to deflate the expandable member by withdrawing the same fixed volume of fluid into the chamber 210.

Figure 15:
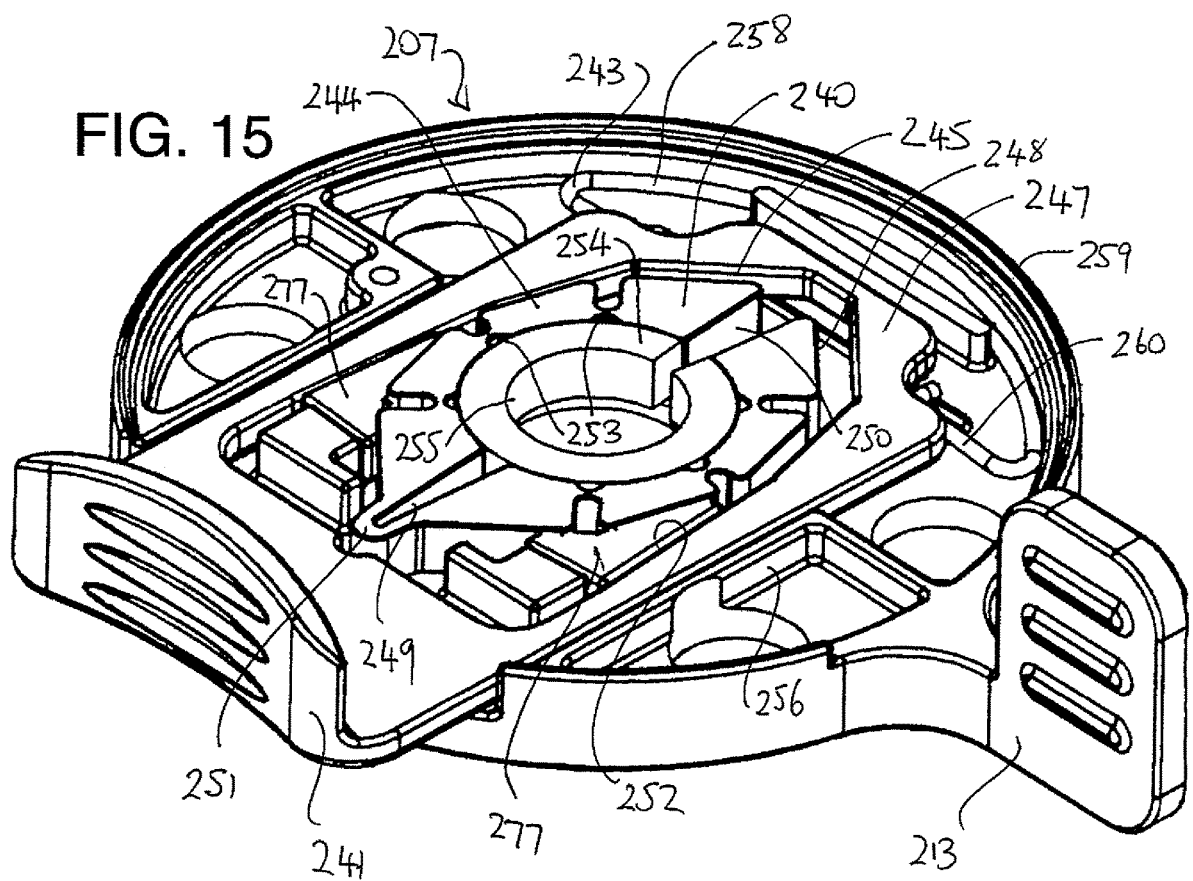
FIG. 15 is an isometric view of one part only of the embodiment of FIG. 12 showing the arrangement for releasably clamping the slidable collar to the trocar.
Figure 17:
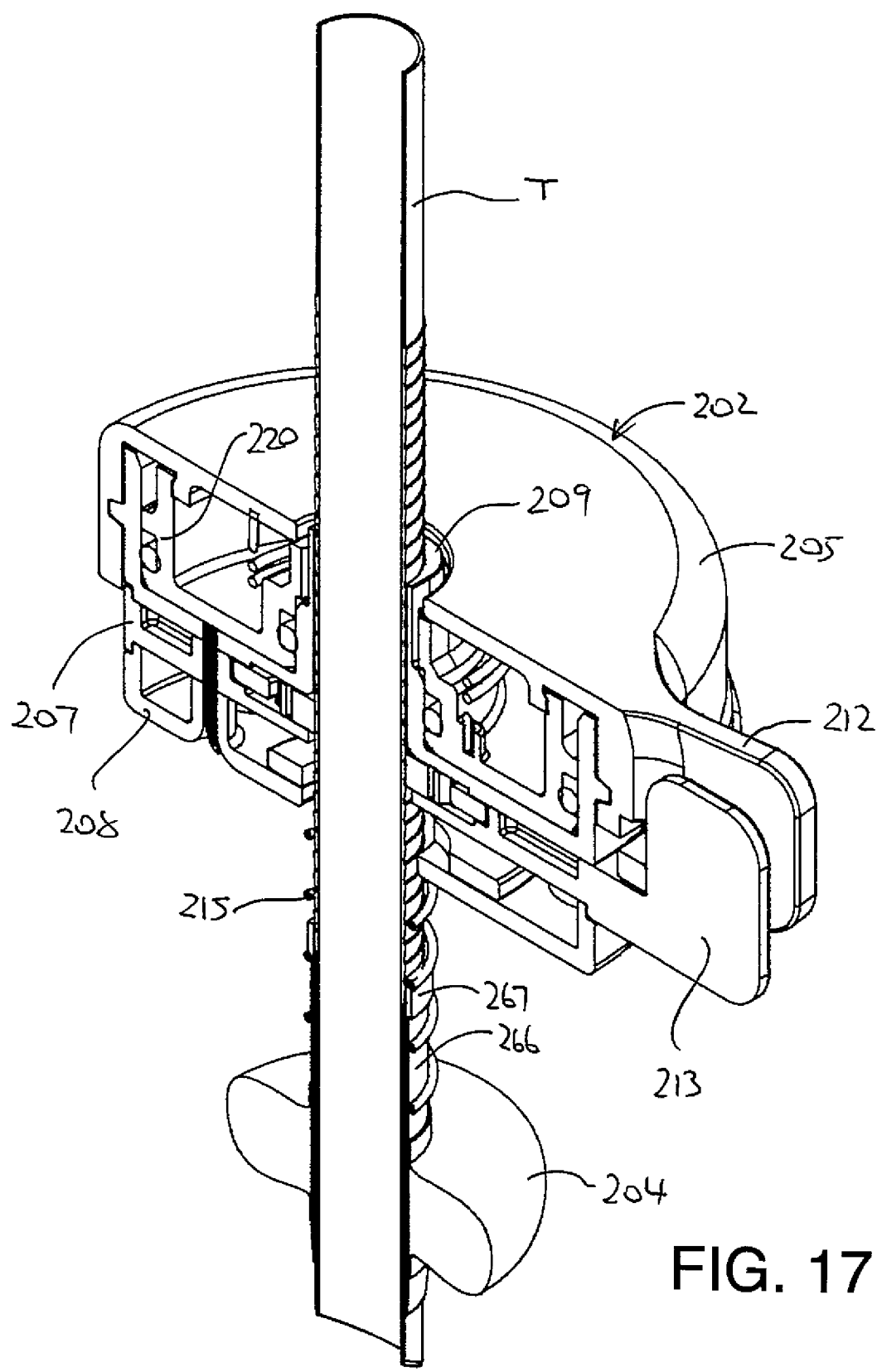
FIG. 17 is an isometric view partly in cross-section similar to that of FIG. 13 showing the inflation system in the final position.

Section 207 is shown in FIG. 15 which provides an arrangement where the annular abutment collar 202 is clamped to the trocar T by a clamp mechanism in the form of a disk member 240 having a manually engageable portion 241 exposed at one side of the annular abutment collar 202 for pressing the disk member 240 in a direction radially away from the trocar against a spring bias. The clamp mechanism 240 is designed so that the collar 202 is clamped to the trocar T until pressure is applied to the release button 241. While the button 241 is in the depressed state, the collar is free to slide along the axis of the trocar. This drawing depicts the mechanism with the button in the partially depressed position.

In the arrangement shown, a metal spring 243 applies a constant force to the button 241 in the direction outwardly from the trocar, in which position the trocar is clamped. The button 241 extends into the interior of the section 207 and includes a generally rectangular tray portion 247 containing a resilient hinged clamp 244. The force from the spring 243 on the button 241 causes the resilient hinged clamp 244 to interfere with the wedge-shaped profiles 245 and 277 in the interior opening 252 of the tray portion 247 of the button 241. The cooperation between the profile 277 and an outer edge 248 of the clamp 240 results in compression of the clamp 240 around the circumference of the trocar. The gaps to 249 and 250 at either end of the clamp 240 close together while clamping around the trocar.

When the user applies sufficient thumb pressure to the button 241 to over-come the force of spring 243, the button 241 will engage the clamp 240 at point 251 causing the hinged clamp 240 to open-up and release its grip around the trocar. The profile of the opening 252 in the tray portion 247 of the button 241 widens allowing the wedges 248 to move apart relative to the clamped position allowing the clamp space to open-up.

Releasing the thumb pressure from button 241 will cause the slidable collar 240 to clamp onto the trocar again. The semi-cylinders 253 around the clamp-trocar interface allow ethylene oxide (ETO) gas to pass through during the sterilization process.

The clamp 240 is formed in a plurality of individually hinged sections surrounding a resilient ring 254 formed of flexible silicone rubber. An inside surface 255 of the ring 254 engages frictionally around the outside surface of the trocar. The individual sections of the clamp ensure that a substantially constant pressure is applied onto the outside surface of the trocar so as to provide an effective clamping action. This avoids the situation where the clamping force is restricted to a certain part or parts of the periphery of the trocar which can lead to an unacceptable clamping force.

Figure 18:
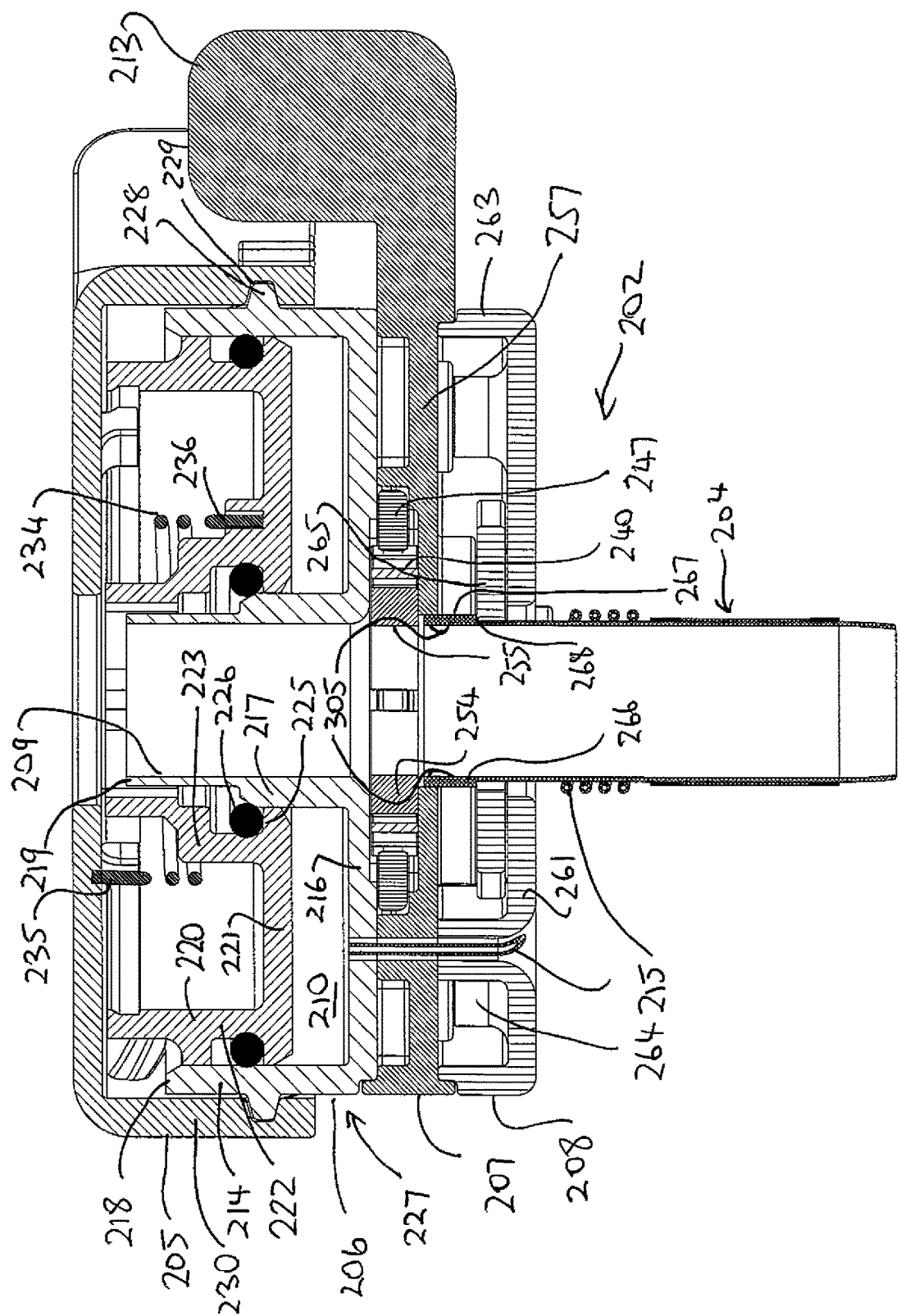
FIG. 18 is a cross-sectional view along the lines 18-18 of the embodiment of FIG. 12 showing the inflation system in a partly inflated position.

The tray 247 is mounted in the annular body defining the section 207 which is molded with the guide walls 256 which guide the sliding action of the button 241 when depressed. The abutment 213 which is part of the pumping mechanism is mounted on the outside surface of the section 207 and this section is fixed and held stationary relative to the trocar by the clamping action and the by its cooperation with the section 208 to which it is attached by fasteners. As shown in FIG. 18, the tray 247 sits on a bottom wall 257 of the section 207 and is prevented from lifting upwardly from the section 207 by its engagement with the underside of the bottom wall 216 of the section 206. The spring 243 includes an arch portion 258 extending around the outer wall 259 of the section 207 together with end tab portions 260 which butt against the end wall of the tray 247. This pushes against the tray, extending the button 241 and pressing the wedges 245 and 277 against the surface 248 of the clamp 240 acting to squeeze it around the ring 254 in the clamping action.

Figure 16:
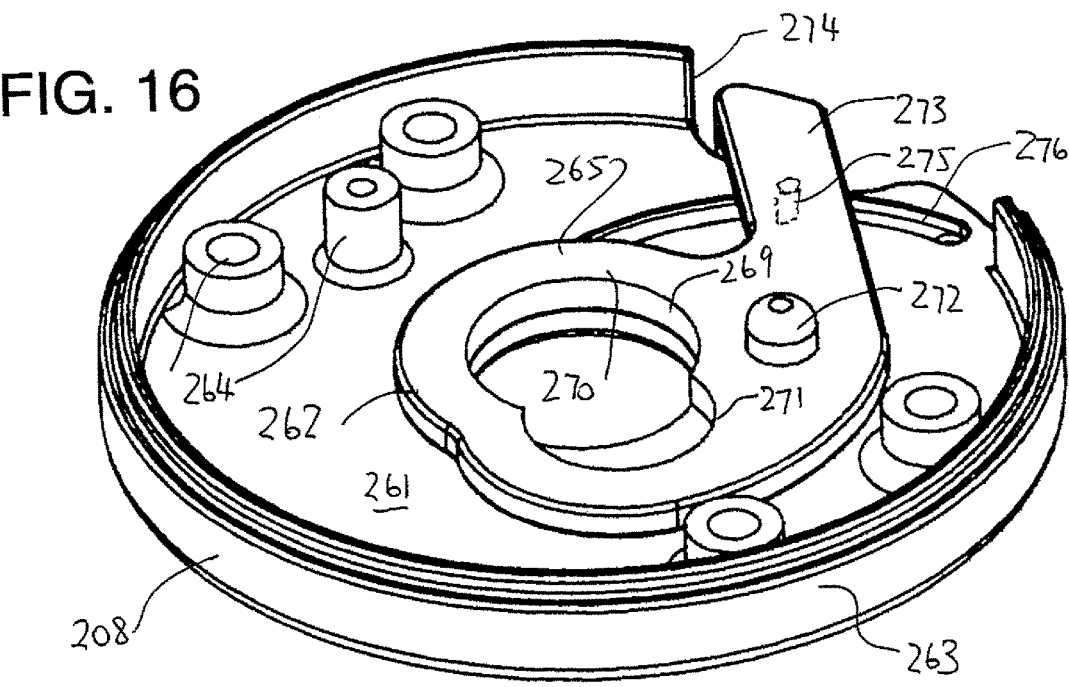
FIG. 16 is an isometric view of one part only of the embodiment of FIG. 12 showing the arrangement for releasably connecting the expandable collar to the slidable collar.

As shown in FIGS. 16 and 18 is provided a connecting component 262 mounted on the annular abutment collar at the section 208 for engaging a portion of the annular expandable member to engage and hold the annular expandable member in engagement with the annular abutment collar. The section 208 comprises a base wall 261 and an upstanding peripheral wall 263 generally matching in diameter the outside surface of the section 207. On the base wall 261 is provided a plurality of annular fixing collars 264 by which the components are clamped together by suitable fasteners. The component 262 acts to clamp together the expandable collar portion and the abutment portion for common insertion of the trocar therethrough. The component 262 comprises a collar 265 which surrounds an upper part 266 of the expandable balloon portion 204. On the top of the upper part 266 is provided an outer band 267 defining a bottom shoulder 268 which sits on the top of the collar 265. An internal opening 269 has a large section 270 on the smaller section 271 where the smaller section clamped closely around the upper part 266 under the band 267. When the component 262 is pivoted around a mounting member 272, this causes the larger section 270 to move to a position around the upper part 266 so that this portion is released from the clamping action allowing the abutment member and the expandable member to move apart.

In some embodiments, the annular expandable member 203 includes a sleeve slightly bigger than the trocar with an internal peripheral rib 305 on the inside surface of the upper part 266 at the band 267 which engages over a rib on the trocar to lock the annular expandable member in place. In other embodiments such as shown in FIGS. 1 to 11, the sleeve of the expandable member is arranged to be tight on the trocar and is held spaced from the trocar by the insert portion from the collar.

In this way the component 262 includes a release member defined by a lever 273 to release the clamping action to allow movement of the expandable member after the expandable member is moved to a required position of the annular expandable member on the trocar. The release member defined by the lever 273 slidable in a slot 274 in the wall 263 is operable to release the connecting component 262 to effect release of the annular expandable member from the annular abutment collar. When released the annular abutment collar is movable longitudinally relative to the annular expandable member such that the annular abutment collar is moved to a position to hold the body wall between the annular abutment collar and the annular expandable member.

The connecting component 262 and the release member 273 are carried on the annular abutment collar 202 at the section 208 and the connecting component 262 includes a surface 271 for engaging upper part 266 of the annular expandable member.

In the arrangement shown the component 262 is mounted for pivotal movement around a mounting pin, however the component can form a disk which slides in and out of the section 208 is a radial direction so that the keyhole shaped slot 270, 271 moves relative to the trocar and the upper part 266 of the expandable member.

A projecting member 275 on the on the underside of the arm 273 cooperates with a slot 276 in the base wall 261 so as to guide and locate the arm in its movement between the two positions defined above. Suitable restrictions can be provided in the slot 276 to actively locate the arm and its two positions.

The keyhole shaped surface 269 of the connecting component surrounds the trocar so that a portion 266 of the annular expandable member projects axially into the interior of the surface to hold the expandable member in place. The surface 269 of the sliding plate 265 forms a ring on the section 208 of the collar 202 defining an opening in the plate or disk 265 to hold and release the portion 266.

Figure 19:
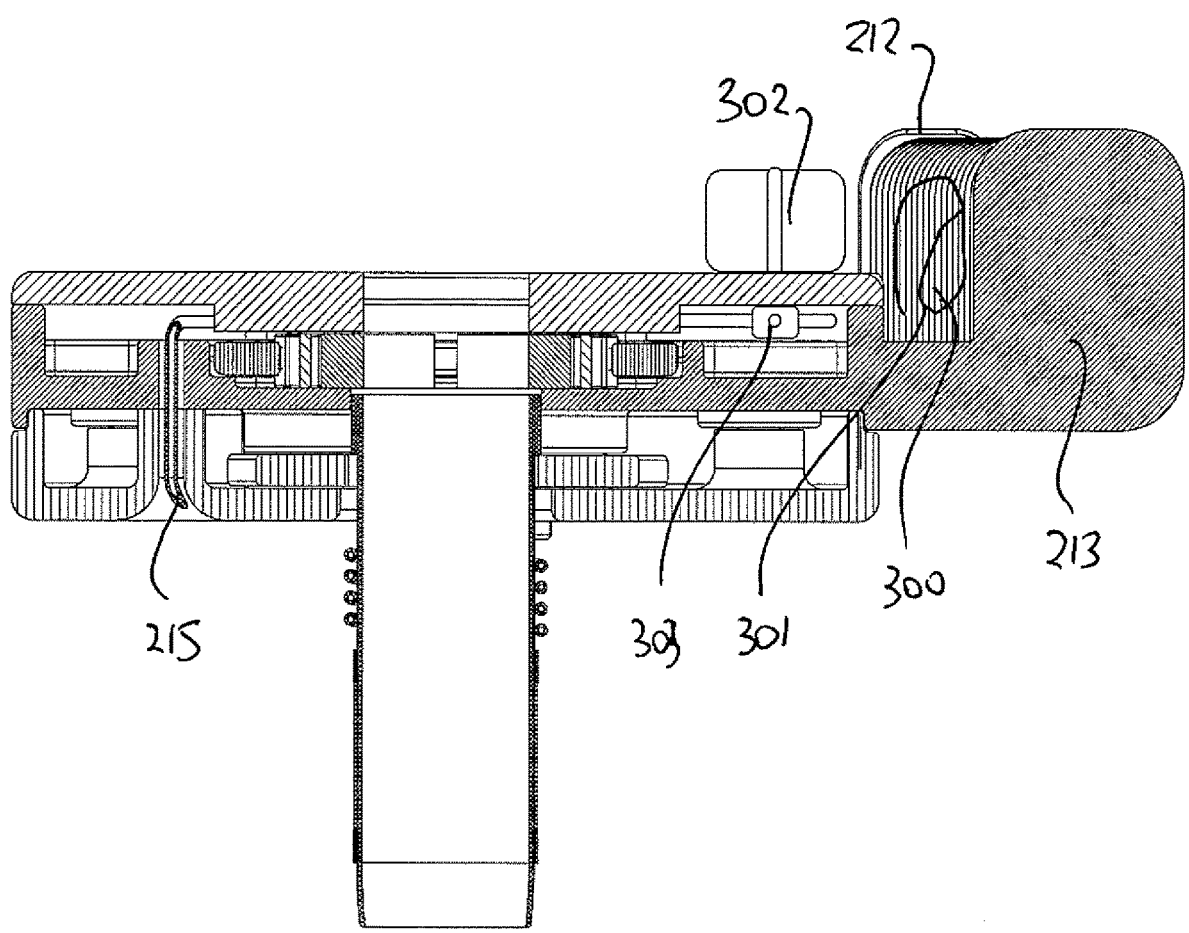
FIG. 19 is a cross-sectional view similar to that of FIG. 18 showing a further embodiment of the invention.
Figure 20:
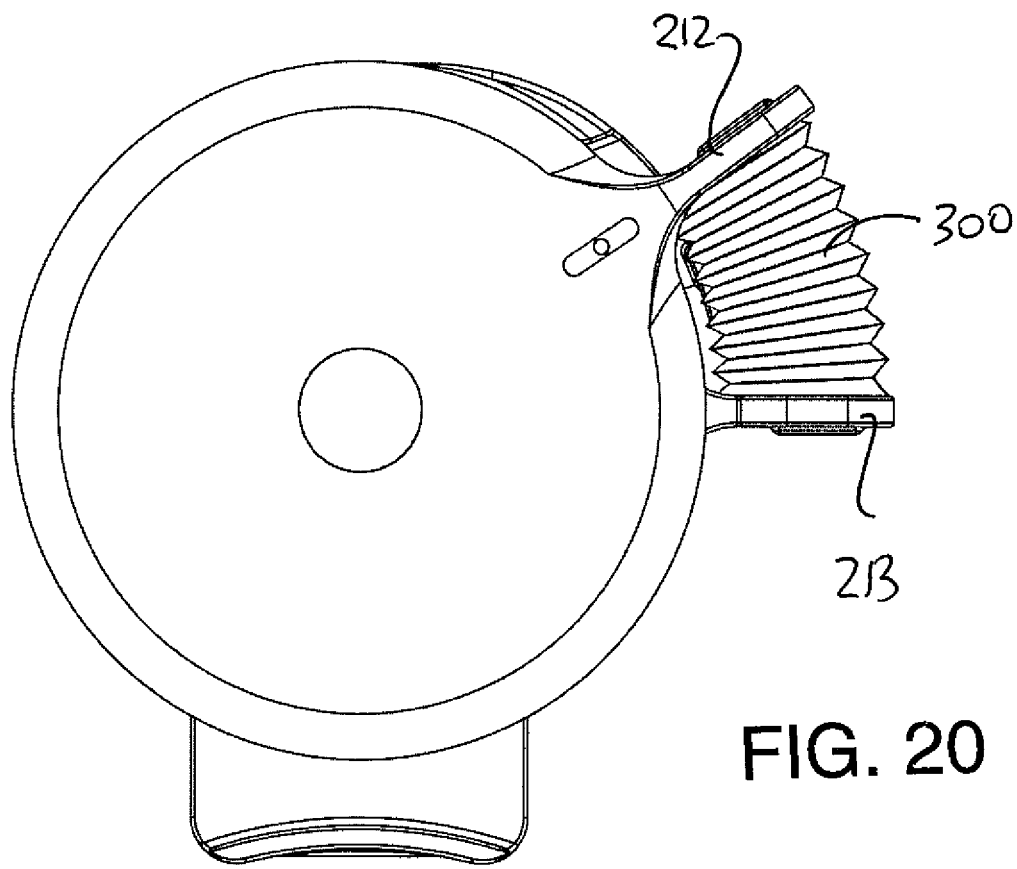
FIG. 20 is a top plan view of the embodiment of FIG. 19.
Figure 21:
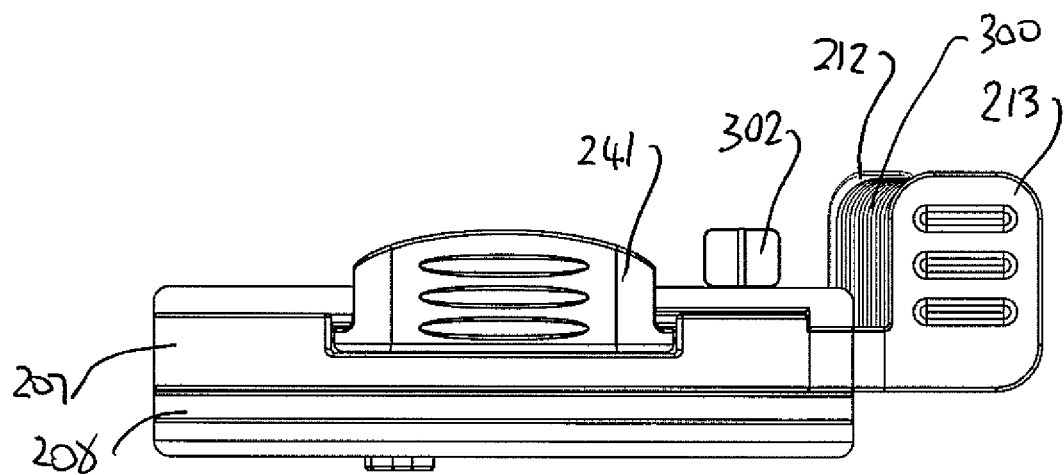
FIG. 21 is a side elevational view of the embodiment of FIG. 19.

In another arrangement shown in FIGS. 19 to 21 the pump defined above by the cylinder and the cooperating piston is replaced by a simple bellows arrangement 300 located between the abutments 212 and 213. In this way, as the abutments 212 and 213 are squeezed together manually, this acts to compress the bellows arrangement 300 which forces air from the interior of the bellows arrangement in to the duct 215. A spring 301 is provided which can be either as the same construction as described above forming a helical coil around the trocar or it can be a simple compression spring 301 located at the bellows and is compressed as the bellows is depressed. This arrangement is a more simple construction avoiding the necessity for the interior components defining the cylinder and the piston walls. As described above it is essential that the interior of any pumping arrangement such as the bellows can be accessed by exterior fluid for a sterilizing action. A valve arrangement 303 is provided which allows entry of the fluid into the bellows, which is then closed during the operation of the bellows. This can be closed by a manually operable member 302 or automatically by a component of the system. In both cases the valve is arranged as a onetime operation device which acts to close off the access to the exterior sterilizing fluid and to connect the bellows to the conduit 215. As described above the bellows when closed provides a fixed volume of air which is pumped from the bellows through the duct into the inflation balloon to ensure inflation to a required level.

The invention claimed is:

1. A support apparatus for use with a tubular device which is elongate and the tubular device extends in a direction axially of the tubular device through a body wall of a patient for supporting the tubular device in a fixed position, the support apparatus comprising:
   an annular expandable member for extending around the tubular device, said annular expandable member being movable in an expansion movement from a collapsed condition radially outwardly of an axis of the tubular device to a predetermined size;
   an annular abutment collar arranged to be received on the tubular device;
   the annular abutment collar being adjustable in an axial direction of the tubular device longitudinally on the tubular device so as to be located at a position thereon;
   a releasable clamping member on the annular abutment collar for locating the annular abutment collar on the tubular device;
   said annular expandable member being arranged while in said collapsed condition to be inserted through an incision in the body wall and expanded when inserted to engage an inside surface of the body wall;
   wherein the annular expandable member is expandable by a fluid supplied by a fluid pump containing the fluid;
   wherein the fluid pump comprises a pair of annular members locating a fluid containing chamber therebetween containing the fluid, the pair of annular members surrounding a central opening through which the tubular device passes;
   one of the pair of annular members being movable in the axial direction toward the other of the pair of annular members to expel the fluid from the fluid containing chamber;
   and wherein there is provided a screw thread interconnecting the pair of annular members so that rotation of said one of the pair of annular members around the axis causes movement in said axial direction.

2. The support apparatus according to claim 1 wherein one of the pair of annular members comprises a cylinder and the other of the annular members comprises a piston defining said fluid containing chamber in the cylinder so that the movement in the axial direction causes the chamber to be reduced in volume expelling the fluid therefrom.

3. The support apparatus according to claim 1 wherein the screw thread is on an outside surface of one of the pair of annular members.

4. A support apparatus for use with a tubular device which is elongate and the tubular device extends in a direction axially of the tubular device through a body wall of a patient for supporting the tubular device in a fixed position, the support apparatus comprising:
   an annular expandable member for extending around the tubular device, said annular expandable member being movable in an expansion movement from a collapsed condition radially outwardly of an axis of the tubular device to a predetermined size;
   an annular abutment collar arranged to be received on the tubular device;

the annular abutment collar being adjustable in an axial direction of the tubular device longitudinally on the tubular device so as to be located at a position thereon;

a releasable clamping member on the annular abutment collar for locating the annular abutment collar on the tubular device;

said annular expandable member being arranged while in said collapsed condition to be inserted through an incision in the body wall and expanded when inserted to engage an inside surface of the body wall;

wherein the annular expandable member is expandable by a fluid supplied by a fluid pump containing the fluid;

wherein the fluid pump comprises a pair of annular members locating a fluid containing chamber therebetween containing the fluid, the pair of annular members surrounding a central opening through which the tubular device passes;

one of the pair of annular members being movable in the axial direction toward the other of the pair of annular members to expel the fluid from the fluid containing chamber;

and wherein there is provided a latch for holding the pair of annular members in fixed position after a volume of fluid is supplied.

5. A support apparatus for use with a tubular device which is elongate and the tubular device extends in a direction axially of the tubular device through a body wall of a patient for supporting the tubular device in a fixed position, the support apparatus comprising:

an annular expandable member for extending around the tubular device, said annular expandable member being movable in an expansion movement from a collapsed condition radially outwardly of an axis of the tubular device to a predetermined size;

an annular abutment collar arranged to be received on the tubular device;

the annular abutment collar being adjustable in an axial direction of the tubular device longitudinally on the tubular device so as to be located at a position thereon;

a releasable clamping member on the annular abutment collar for locating the annular abutment collar on the tubular device;

said annular expandable member being arranged while in said collapsed condition to be inserted through an incision in the body wall and expanded when inserted to engage an inside surface of the body wall;

wherein the annular expandable member is expandable by a fluid supplied by a fluid pump containing the fluid;

wherein the fluid pump comprises a pair of annular members locating a fluid containing chamber therebetween containing the fluid, the pair of annular members surrounding a central opening through which the tubular device passes;

one of the pair of annular members being movable in the axial direction toward the other of the pair of annular members to expel the fluid from the fluid containing chamber;

and wherein the pair of annular members include a first finger engagement abutment and a second thumb engagement abutment, each extending generally radially outwardly from the axis with the first finger engagement abutment and the second thumb engagement abutment being relatively rotatable angularly around the axis toward one another to expel the fluid from the fluid containing chamber.

6. The support apparatus according to claim 1 wherein there is provided a spring which moves the pair of annular members in a return direction opposite to said axial direction to a retracted position to deflate the annular expandable member.

7. The support apparatus according to claim 6 wherein the spring is located between the pair of annular members.

8. The support apparatus according to claim 6 wherein the spring is wound around the axis.

9. The support apparatus according to claim 1 wherein there is provided a connecting component mounted on the annular abutment collar for engaging a portion of the annular expandable member to engage and hold the annular expandable member in engagement with the annular abutment collar and a release member operable to release the connecting component to effect release of the annular expandable member from the annular abutment collar.

10. The support apparatus according to claim 9 wherein the connecting component and the release member are carried on the annular abutment collar and the connecting component includes a surface for engaging a portion of the annular expandable member.

11. The support apparatus according to claim 10 wherein the surface of the connecting component surrounds the axis so that said portion of the annular expandable member projects axially into engagement with the surface.

12. The support apparatus according to claim 1 wherein said releasable clamping member comprises a disk member having an inner surface surrounding the tubular device and a manually engageable portion exposed at one side of the annular abutment collar for retracting the disk member in a direction radially away from the tubular device against a spring bias.

13. The support apparatus according to claim 12 wherein the disk member surrounds the tubular device and includes components applying a force to the tubular device at all points therearound.

14. A support apparatus for use with a tubular device which is elongate and the tubular device extends in a direction axially of the tubular device through a body wall of a patient for supporting the tubular device in a fixed position, the support apparatus comprising:

an annular expandable member for extending around the tubular device, said annular expandable member being movable in an expansion movement from a collapsed condition radially outwardly of an axis of the tubular device to a predetermined size;

an annular abutment collar arranged to be received on the tubular device;

the annular abutment collar being adjustable in an axial direction of the tubular device longitudinally on the tubular device so as to be located at a position thereon;

a releasable clamping member on the annular abutment collar for locating the annular abutment collar on the tubular device;

said annular expandable member being arranged while in said collapsed condition to be inserted through an incision in the body wall and expanded when inserted to engage an inside surface of the body wall;

wherein the annular expandable member is expandable by an inflation fluid supplied by a fluid pump containing the inflation fluid;

wherein the fluid pump comprises a pair of members locating a chamber therebetween containing the inflation fluid;

the pair of members including a first finger engagement abutment and a second thumb engagement abutment, each extending generally radially outwardly from the axis;

the first finger engagement abutment and the second thumb engagement abutment being relatively rotatable angularly around the axis toward one another to expel the inflation fluid from the chamber.

15. The support apparatus according to claim 14 wherein there is provided a latch for holding the pair of members in fixed position after a volume of fluid is supplied.

16. The support apparatus according to claim 14 wherein there is provided a connecting component mounted on the annular abutment collar for engaging a portion of the annular expandable member to engage and hold the annular expandable member in engagement with the annular abutment collar and a release member operable to release the connecting component to effect release of the annular expandable member from the annular abutment collar.

* * * * *